United States Patent
Kishi et al.

(10) Patent No.: US 6,525,220 B2
(45) Date of Patent: Feb. 25, 2003

(54) INTERMEDIATES FOR THE SYNTHESIS OF BENZIMIDAZOLE DERIVATIVES AND A PROCESS FOR THE PREPARATION THEREOF

(75) Inventors: Naoyuki Kishi, Fujisawa (JP); Yoshitaka Nakamura, Yokohama (JP); Narumi Abe, Hiratsuka (JP); Toyonori Takebayashi, Yokohama (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/025,366

(22) Filed: Dec. 19, 2001

(65) Prior Publication Data
US 2003/0008907 A1 Jan. 9, 2003

Related U.S. Application Data

(63) Continuation of application No. PCT/JP00/04213, filed on Jun. 27, 2000.

(30) Foreign Application Priority Data

Jun. 28, 1999 (JP) ............................................. 11-181898

(51) Int. Cl.[7] ......................... C07C 27/28; C07C 269/06
(52) U.S. Cl. ...................................... 564/300; 564/305
(58) Field of Search .................................. 564/300, 305

(56) References Cited

U.S. PATENT DOCUMENTS 5,886,014 A    3/1999   Fujita et al.

FOREIGN PATENT DOCUMENTS

| EP | 0 745 600 A1 | 12/1996 |
| EP | 1 022 272 A1 | 7/2000 |

OTHER PUBLICATIONS

Qunbun, et al., Bioorg. Med. Chem. Lett., 1994, vol. 4, No. 24, p. 2871–2876.
Bianchi, et al. Tetrahedron, 1974, vol. 30, No. 16, p. 2765–2771.

*Primary Examiner*—Joseph K. McKane
*Assistant Examiner*—Andrea D. Small
(74) *Attorney, Agent, or Firm*—Frishauf, Holtz, Goodman & Chick, P.C.

(57) ABSTRACT

This invention provides a process for the preparation of a benzimidazole derivative (I) or a pharmaceutically acceptable salt thereof,

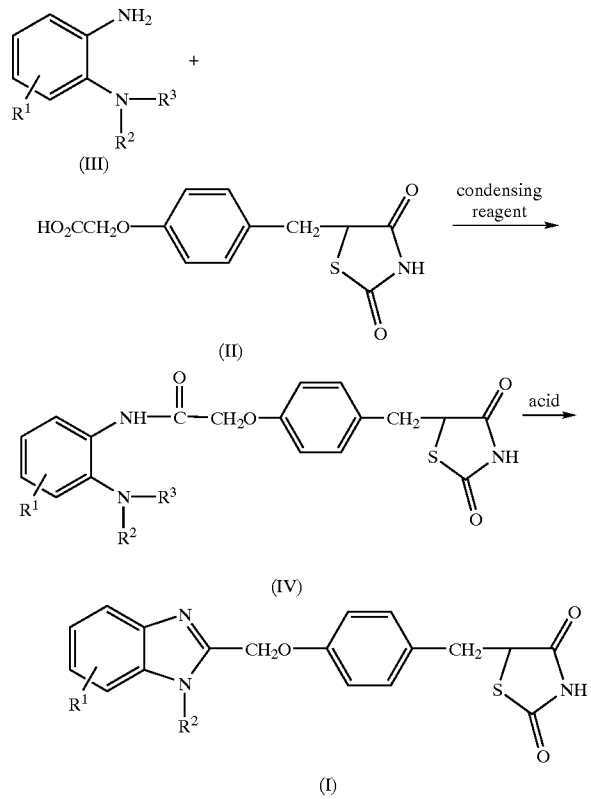

wherein $R^1$ is $C_1$–$C_6$ alkyl, $C_1$–$C_6$ alkoxyl, etc., $R^2$ is $C_1$–$C_6$ alkyl, and $R^3$ is hydrogen or a protecting group, which exhibits excellent hyopoglycemic action, said process comprising condensation of an amine derivative (III) with a carboxylic acid derivatives (II) to afford a compound (IV), followed by cyclization of compound (IV) in the presence of an acid.

6 Claims, No Drawings

INTERMEDIATES FOR THE SYNTHESIS OF BENZIMIDAZOLE DERIVATIVES AND A PROCESS FOR THE PREPARATION THEREOF

This application is a continuation application of International Application PCT/JP00/04213 filed Jun. 27, 2000 (not published in English).

FIELD OF THE INVENTION

This invention relates to a process for the preparation of benzimidazole derivatives and pharmaceutically acceptable salts thereof exhibiting excellent hypoglycemic action and intermediates for their synthesis.

BACKGROUND OF THE INVENTION

Some benzimidazole derivatives having hypoglycemic activity and pharmaceutically acceptable salts thereof and a process for the preparation of these derivatives are disclosed in Japanese Patent Application Publication Hei-9-295970 (European Patent Application Publication number 00745600 and U.S. Pat. No. 5,886,014).

The known method for the preparation of the benzimidazole derivatives comprises:
1) protection of the amino group of a nitroaniline derivative,

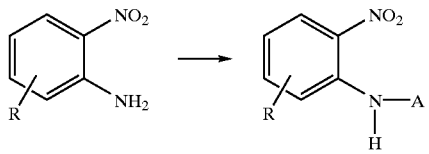

(wherein A is an amino protecting group, R is methoxy and the like);
2) a few reactions via the amino-protected nitroaniline derivative to afford an N-methyl-1,2-phenylenediamine derivative, and
3) reaction of the N-methyl-1,2-phenylenediamine derivative by heating with a methoxycarbonylmethyloxybenzylthiazolidinone derivative in the presence of an acid to produce a benzimidazole derivative shown below.

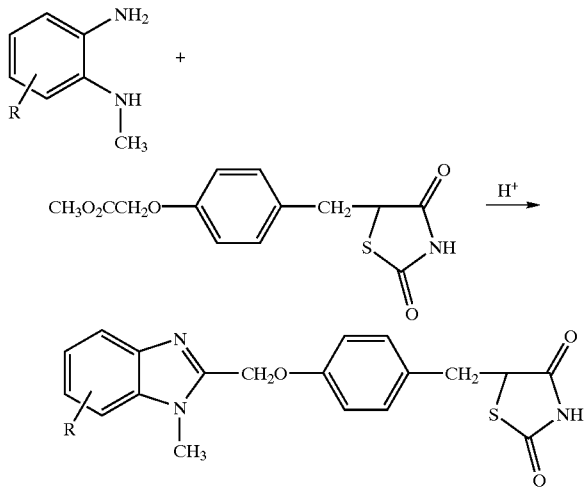

(wherein R is methoxy and the like)
In the method disclosed in Japanese Patent Application Publication Hei-9-295970 (U.S. Pat. No. 5,886,014), the overall yields of the benzimidazole derivatives, especially the two reactions shown above, are low and this method can not practically be used. A practical large scale method for the synthesis of the benzimidazole derivatives is needed, in which method the product is of good purity and is obtained by easy procedures using cheap starting materials, and in good yield.

SUMMARY OF THE INVENTION

We made many efforts in order to find a good synthetic method for a large scale preparation of the benzimidazole derivatives for a long time. We found a good method for the preparation which comprises the reaction of a group of carboxylic acid derivatives with a group of optionally protected amine derivatives.

This invention provides a process for the preparation of the benzimidazole derivatives exhibiting excellent hypoglycemic action or a pharmaceutically acceptable salt thereof and their important synthetic intermediates.

DETAILED DESCRIPTION OF THE INVENTION

This invention is directed to synthetic intermediates of formulae [1], [2] and [3] and processes for preparation illustrated in [4] and [5].

[1] A compound of formula (1) (which is referred to as compound (1) hereinafter) or a pharmaceutically acceptable salt thereof,

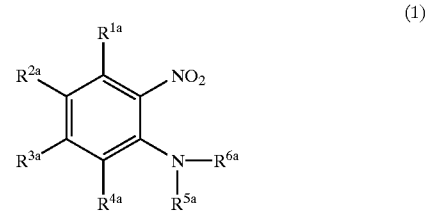

(1)

(wherein $R^{1a}$, $R^{2a}$, $R^{3a}$ and $R^{4a}$ are each independently hydrogen, hydroxyl, $C_1$–$C_6$ alkyl, $C_1$–$C_6$ alkoxy, benzyloxy, acetoxy, trifluoromethyl or halogen, and $R^{5a}$ and $R^{6a}$ are each independently an amino protecting group).

Preferable compounds of formula (1) are:
[1-1] compounds and pharmaceutically acceptable salts thereof according to [1] wherein $R^{5a}$ and $R^{6a}$ are each independently t-butoxycarbonyl, benzyloxycarbonyl, p-methoxybenzyloxycarbonyl or p-bromobenzyloxycarbonyl;
[1-2] compounds and pharmaceutically acceptable salts thereof according to [1] wherein $R^{5a}$ and $R^{6a}$ are each t-butoxycarbonyl;
[1-3] compounds and pharmaceutically acceptable salts thereof according to any one of [1], [1-1] or [1-2] wherein $R^{1a}$, $R^{2a}$, $R^{3a}$ and $R^{4a}$ are each independently hydrogen or $C_1$–$C_4$ alkoxy;
[1-4] compounds and pharmaceutically acceptable salts thereof according to any one of [1], [1-1] or [1-2] wherein $R^{1a}$, $R^{2a}$, $R^{3a}$ and $R^{4a}$ are each independently hydrogen or methoxy; and
[1-5] compounds and pharmaceutically acceptable salts thereof according to [1] wherein $R^{1a}$, $R^{2a}$ and $R^{4a}$ are each hydrogen, $R^{3a}$ is methoxy, and $R^{5a}$ and $R^{6a}$ are each t-butoxycarbonyl.

The $C_1$–$C_6$ alkyl group of compound (1) is a $C_1$–$C_6$ straight or branched chain alkyl group, for example, methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl, preferably $C_1$–$C_4$ alkyl, more preferably methyl or ethyl and most preferably methyl.

The $C_1$–$C_6$ alkoxyl group of compound (1) is a $C_1$–$C_6$ alkyl described above group attached to an oxygen atom, for example, methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy, preferably $C_1$–$C_4$ alkoxy, more preferably methoxy or ethoxy and most preferably methoxy.

The halogen atom of compound (1) is, for example, fluorine, chlorine, bromine or iodine, preferably fluorine, chlorine or bromine.

The amino protecting group in the definition of compound (1) is, for example, t-butoxycarbonyl; trityl; $(C_6$–$C_{10})$aryl-methyl, which is optionally substituted with $C_1$–$C_6$ alkyl, $C_1$–$C_6$ alkoxy or halogen, such as benzyl, methylbenzyl, methoxybenzyl, chlorobenzyl, bromobenzyl and naphthyl-methyl; or $(C_6$–$C_{10})$aryl-methyloxycarbonyl, which is optionally substituted with $C_1$–$C_6$ alkyl, $C_1$–$C_6$ alkoxy or halogen, such as benzyloxycarbonyl, methylbenzyloxycarbonyl, methoxybenzyloxycarbonyl, chlorobenzyloxycarbonyl, bromobenzyloxycarbonyl and naphthylmethyloxycarbonyl. t-Butoxycarbonyl, benzyl, p-methoxybenzyl, p-bromobenzyl, benzyloxycarbonyl, p-methoxybenzyloxycarbonyl and p-bromobenzyloxycarbonyl are preferred; t-butoxycarbonyl, benzyloxycarbonyl, p-methoxybenzyloxycarbonyl and p-bromobenzyloxycarbonyl are more preferred and t-butoxycarbonyl is particularly preferred.

In compound (1), preferably $R^{1a}$, $R^{2a}$, $R^{3a}$ and $R^{4a}$ are each independently hydrogen or $C_1$–$C_4$ alkoxy; more preferably $R^{1a}$, $R^{2a}$, $R^{3a}$ and $R^{4a}$ are each independently hydrogen or methoxy; and most preferably $R_{1a}$, $R^{2a}$ and $R^{4a}$ are each hydrogen and most preferably $R^{3a}$ is methoxy; and preferably $R^{5a}$ and $R^{6a}$ are each independently t-butoxycarbonyl, benzyloxycarbonyl, p-methoxybenzyloxycarbonyl or p-bromobenzyloxycarbonyl and more preferably $R^{5a}$ and $R^{6a}$ are each t-butoxycarbonyl.

Pharmaceutically acceptable salts in the definition of salts of compound (1) are, for example, hydrohalogenides such as hydrofluoride, hydrochloride, hydrobromide and hydroiodide; perchlorates; sulfates; phosphates; carbonates; $C_1$–$C_6$ alkylsulfonates, which are optionally substituted with fluorines, such as methanesulfonate, tifluoromethanesulfonate, ethanesulfonate, pentafluoroethanesulfonate, propanesulfonate, butanesulfonate, pentanesulfonate and hexanesulfonate; $C_6$–$C_{10}$ arylsulfonates such as benzenesulfonate and p-toluenesulfonate; carboxylic acid salts such as acetate, propionate, butyrate, benzoate, fumarate, maleate, succinate, citrate, tartarate, oxalate and malonate; and amino acid addition salts such as glutamate and aspartate. Hydrochlorides, sulfates, and carboxylic acid salts are more preferred, and hydrochlorides are particularly preferred. The pharmaceutically acceptable salts of this invention include hydrates and solvates of organic solvents.

Typical compounds of formula (1) are exemplified in the Tables 1 to 4. Throughout the tables the following abbreviations are used with the following meaning:

Exp. Comp. No: Exemplification compound number

Me: methyl, Et: ethyl, Pr: propyl, iPr: isopropyl, Bu: butyl, iBu: isobutyl, sBu: secondary butyl, tBu: tertiary butyl, Bz: benzyl, Ac: acetyl, Boc: tertiary butoxycarbonyl, Z: benzyloxycarbonyl, Moz: p-methoxybenzyloxycarbonyl, 4BrZ: p-bromobenzyloxycarbonyl

TABLE 1

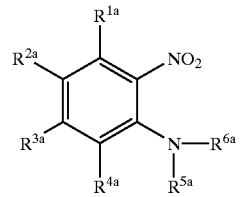

(1)

| Exp. Comp. No. | $R^{1a}$ | $R^{2a}$ | $R^{3a}$ | $R^{4a}$ | $R^{5a} = R^{6a}$ |
|---|---|---|---|---|---|
| 1-1 | H | H | H | H | Boc |
| 1-2 | H | H | MeO | H | Boc |
| 1-3 | H | H | EtO | H | Boc |
| 1-4 | H | H | PrO | H | Boc |
| 1-5 | H | H | iPrO | H | Boc |
| 1-6 | H | H | BuO | H | Boc |
| 1-7 | H | H | iBuO | H | Boc |
| 1-8 | H | H | sBuO | H | Boc |
| 1-9 | H | H | tBuO | H | Boc |
| 1-10 | H | H | BuO | H | Boc |
| 1-11 | H | H | BzO | H | Boc |
| 1-12 | H | MeO | Me | H | Boc |
| 1-13 | H | MeO | Br | H | Boc |
| 1-14 | H | EtO | F | H | Boc |
| 1-15 | H | F | H | F | Boc |
| 1-16 | H | H | F | H | Boc |
| 1-17 | H | Cl | Me | H | Boc |
| 1-18 | H | Cl | Et | H | Boc |
| 1-19 | H | Et | H | H | Boc |
| 1-20 | H | H | Br | H | Boc |
| 1-21 | H | $CF_3$ | H | Br | Boc |
| 1-22 | H | $CF_3$ | H | Cl | Boc |
| 1-23 | H | H | H | $CF_3$ | Boc |
| 1-24 | H | H | $CF_3$ | H | Boc |
| 1-25 | H | Br | Me | Me | Boc |
| 1-26 | H | F | Cl | H | Boc |
| 1-27 | H | Br | H | Me | Boc |
| 1-28 | H | H | tBu | H | Boc |
| 1-29 | H | OH | H | H | Boc |
| 1-30 | H | H | H | Me | Boc |
| 1-31 | H | H | Cl | Cl | Boc |
| 1-32 | H | F | F | F | Boc |
| 1-33 | H | Br | BzO | H | Boc |
| 1-34 | H | H | H | Cl | Boc |
| 1-35 | H | Me | OH | Me | Boc |
| 1-36 | H | MeO | H | H | Boc |
| 1-37 | H | EtO | H | H | Boc |
| 1-38 | H | PrO | H | H | Boc |
| 1-39 | H | iPrO | H | H | Boc |
| 1-40 | H | BuO | H | H | Boc |
| 1-41 | H | iBuO | H | H | Boc |
| 1-42 | H | sBuO | H | H | Boc |
| 1-43 | H | tBuO | H | H | Boc |
| 1-44 | H | BuO | H | H | Boc |
| 1-45 | H | BzO | H | H | Boc |
| 1-46 | H | Me | MeO | H | Boc |
| 1-47 | H | Br | MeO | H | Boc |
| 1-48 | H | F | EtO | H | Boc |
| 1-49 | F | H | F | H | Boc |
| 1-50 | H | F | H | H | Boc |
| 1-51 | H | Me | Cl | H | Boc |
| 1-52 | H | Et | Cl | H | Boc |
| 1-53 | H | H | Et | H | Boc |

TABLE 1-continued (1)

$$\begin{array}{c}\text{R}^{1a}\\\text{R}^{2a}\diagdown\diagup\text{NO}_2\\|\phantom{xxx}|\\\text{R}^{3a}\diagup\diagdown\text{N}-\text{R}^{6a}\\\text{R}^{4a}\phantom{xx}\text{R}^{5a}\end{array}$$

| Exp. Comp. No. | $R^{1a}$ | $R^{2a}$ | $R^{3a}$ | $R^{4a}$ | $R^{5a} = R^{6a}$ |
|---|---|---|---|---|---|
| 1-54 | H | Br | H | H | Boc |
| 1-55 | Br | H | CF$_3$ | H | Boc |
| 1-56 | Cl | H | CF$_3$ | H | Boc |
| 1-57 | CF$_3$ | H | H | H | Boc |
| 1-58 | H | CF$_3$ | H | H | Boc |
| 1-59 | Me | Me | Br | H | Boc |
| 1-60 | H | Cl | F | H | Boc |
| 1-61 | H | Br | H | Me | Boc |
| 1-62 | H | tBu | H | H | Boc |
| 1-63 | H | H | OH | H | Boc |
| 1-64 | Me | H | H | H | Boc |
| 1-65 | Cl | Cl | H | H | Boc |
| 1-66 | F | F | F | H | Boc |
| 1-67 | H | BzO | Br | H | Boc |
| 1-68 | Cl | H | H | H | Boc |
| 1-69 | Me | OH | Me | H | Boc |
| 1-70 | Me | OH | Me | Me | Boc |
| 1-71 | Me | OH | Me | Me | Boc |
| 1-72 | Me | AcO | Me | Me | Boc |

TABLE 2

| Exp. Comp.No. | $R^{1a}$ | $R^{2a}$ | $R^{3a}$ | $R^{4a}$ | $R^{5a} = R^{6a}$ |
|---|---|---|---|---|---|
| 2-1 | H | H | H | H | Z |
| 2-2 | H | H | MeO | H | Z |
| 2-3 | H | H | EtO | H | Z |
| 2-4 | H | H | PrO | H | Z |
| 2-5 | H | H | iPrO | H | Z |
| 2-6 | H | H | BuO | H | Z |
| 2-7 | H | H | iBuO | H | Z |
| 2-8 | H | H | sBuO | H | Z |
| 2-9 | H | H | tBuO | H | Z |
| 2-10 | H | H | BuO | H | Z |
| 2-11 | H | H | BzO | H | Z |
| 2-12 | H | MeO | Me | H | Z |
| 2-13 | H | MeO | Br | H | Z |
| 2-14 | H | EtO | F | H | Z |
| 2-15 | H | F | H | F | Z |
| 2-16 | H | H | F | H | Z |
| 2-17 | H | Cl | Me | H | Z |
| 2-18 | H | Cl | Et | H | Z |
| 2-19 | H | Et | H | H | Z |
| 2-20 | H | H | Br | H | Z |
| 2-21 | H | CF$_3$ | H | Br | Z |
| 2-22 | H | CF$_3$ | H | Cl | Z |
| 2-23 | H | H | H | CF$_3$ | Z |
| 2-24 | H | H | CF$_3$ | H | Z |
| 2-25 | H | Br | Me | Me | Z |
| 2-26 | H | F | Cl | H | Z |
| 2-27 | H | Br | H | Me | Z |
| 2-28 | H | H | tBu | H | Z |
| 2-29 | H | OH | H | H | Z |
| 2-30 | H | H | H | Me | Z |
| 2-31 | H | H | Cl | Cl | Z |
| 2-32 | H | F | F | F | Z |
| 2-33 | H | Br | BzO | H | Z |
| 2-34 | H | H | H | Cl | Z |
| 2-35 | H | Me | OH | Me | Z |
| 2-36 | H | MeO | H | H | Z |
| 2-37 | H | EtO | H | H | Z |

TABLE 2-continued

| Exp. Comp.No. | $R^{1a}$ | $R^{2a}$ | $R^{3a}$ | $R^{4a}$ | $R^{5a} = R^{6a}$ |
|---|---|---|---|---|---|
| 2-38 | H | PrO | H | H | Z |
| 2-39 | H | iPrO | H | H | Z |
| 2-40 | H | BuO | H | H | Z |
| 2-41 | H | iBuO | H | H | Z |
| 2-42 | H | sBuO | H | H | Z |
| 2-43 | H | tBuO | H | H | Z |
| 2-44 | H | BuO | H | H | Z |
| 2-45 | H | BzO | H | H | Z |
| 2-46 | H | Me | MeO | H | Z |
| 2-47 | H | Br | MeO | H | Z |
| 2-48 | H | F | EtO | H | Z |
| 2-49 | F | H | F | H | Z |
| 2-50 | H | F | H | H | Z |
| 2-51 | H | Me | Cl | H | Z |
| 2-52 | H | Et | Cl | H | Z |
| 2-53 | H | H | Et | H | Z |
| 2-54 | H | Br | H | H | Z |
| 2-55 | Br | H | CF$_3$ | H | Z |
| 2-56 | Cl | H | CF$_3$ | H | Z |
| 2-57 | CF$_3$ | H | H | H | Z |
| 2-58 | H | CF$_3$ | H | H | Z |
| 2-59 | Me | Me | Br | H | Z |
| 2-60 | H | Cl | F | H | Z |
| 2-61 | H | Br | H | Me | Z |
| 2-62 | H | tBu | H | H | Z |
| 2-63 | H | H | OH | H | Z |
| 2-64 | Me | H | H | H | Z |
| 2-65 | Cl | Cl | H | H | Z |
| 2-66 | F | F | F | H | Z |
| 2-67 | H | BzO | Br | H | Z |
| 2-68 | Cl | H | H | H | Z |
| 2-69 | Me | OH | Me | H | Z |
| 2-70 | Me | OH | Me | Me | Z |
| 2-71 | Me | OH | Me | Me | Z |
| 2-72 | Me | AcO | Me | Me | Z |

TABLE 3

| Exp. Comp.No. | $R^{1a}$ | $R^{2a}$ | $R^{3a}$ | $R^{4a}$ | $R^{5a} = R^{6a}$ |
|---|---|---|---|---|---|
| 3-1 | H | H | H | H | Moz |
| 3-2 | H | H | MeO | H | Moz |
| 3-3 | H | H | EtO | H | Moz |
| 3-4 | H | H | Pro | H | Moz |
| 3-5 | H | H | iPrO | H | Moz |
| 3-6 | H | H | BuO | H | Moz |
| 3-7 | H | H | iBuO | H | Moz |
| 3-8 | H | H | sBuO | H | Moz |
| 3-9 | H | H | tBuO | H | Moz |
| 3-10 | H | H | BuO | H | Moz |
| 3-11 | H | H | BzO | H | Moz |
| 3-12 | H | MeO | Me | H | Moz |
| 3-13 | H | MeO | Br | H | Moz |
| 3-14 | H | EtO | F | H | Moz |
| 3-15 | H | F | H | F | Moz |
| 3-16 | H | H | F | H | Moz |
| 3-17 | H | Cl | Me | H | Moz |
| 3-18 | H | Cl | Et | H | Moz |
| 3-19 | H | Et | H | H | Moz |
| 3-20 | H | H | Br | H | Moz |
| 3-21 | H | CF$_3$ | H | Br | Moz |
| 3-22 | H | CF$_3$ | H | Cl | Moz |
| 3-23 | H | H | H | CF$_3$ | Moz |
| 3-24 | H | H | CF$_3$ | H | Moz |
| 3-25 | H | Br | Me | Me | Moz |
| 3-26 | H | F | Cl | H | Moz |
| 3-27 | H | Br | H | Me | Moz |
| 3-28 | H | H | tBu | H | Moz |
| 3-29 | H | OH | H | H | Moz |
| 3-30 | H | H | H | Me | Moz |
| 3-31 | H | H | Cl | Cl | Moz |
| 3-32 | H | F | F | F | Moz |

TABLE 3-continued

| Exp. Comp.No. | $R^{1a}$ | $R^{2a}$ | $R^{3a}$ | $R^{4a}$ | $R^{5a} = R^{6a}$ |
|---|---|---|---|---|---|
| 3-33 | H | Br | BzO | H | Moz |
| 3-34 | H | H | H | Cl | Moz |
| 3-35 | H | Me | OH | Me | Moz |
| 3-36 | H | MeO | H | H | Moz |
| 3-37 | H | EtO | H | H | Moz |
| 3-38 | H | PrO | H | H | Moz |
| 3-39 | H | iPrO | H | H | Moz |
| 3-40 | H | BuO | H | H | Moz |
| 3-41 | H | iBuO | H | H | Moz |
| 3-42 | H | sBuO | H | H | Moz |
| 3-43 | H | tBuO | H | H | Moz |
| 3-44 | H | BuO | H | H | Moz |
| 3-45 | H | BzO | H | H | Moz |
| 3-46 | H | Me | MeO | H | Moz |
| 3-47 | H | Br | MeO | H | Moz |
| 3-48 | H | F | EtO | H | Moz |
| 3-49 | F | H | F | H | Moz |
| 3-50 | H | F | H | H | Moz |
| 3-51 | H | Me | Cl | H | Moz |
| 3-52 | H | Et | Cl | H | Moz |
| 3-53 | H | H | Et | H | Moz |
| 3-54 | H | Br | H | H | Moz |
| 3-55 | Br | H | $CF_3$ | H | Moz |
| 3-56 | Cl | H | $CF_3$ | H | Moz |
| 3-57 | $CF_3$ | H | H | H | Moz |
| 3-58 | H | $CF_3$ | H | H | Moz |
| 3-59 | Me | Me | Br | H | Moz |
| 3-60 | H | Cl | F | H | Moz |
| 3-61 | H | Br | H | Me | Moz |
| 3-62 | H | tBu | H | H | Moz |
| 3-63 | H | H | OH | H | Moz |
| 3-64 | Me | H | H | H | Moz |
| 3-65 | Cl | Cl | H | H | Moz |
| 3-66 | F | F | F | H | Moz |
| 3-67 | H | BzO | Br | H | Moz |
| 3-68 | Cl | H | H | H | Moz |
| 3-69 | Me | OH | Me | H | Moz |
| 3-70 | Me | OH | Me | Me | Moz |
| 3-71 | Me | OH | Me | Me | Moz |
| 3-72 | Me | AcO | Me | Me | Moz |

TABLE 4

| Exp. Comp.No. | $R^{1a}$ | $R^{2a}$ | $R^{3a}$ | $R^{4a}$ | $R^{5a} = R^{6a}$ |
|---|---|---|---|---|---|
| 4-1 | H | H | H | H | 4BrZ |
| 4-2 | H | H | MeO | H | 4BrZ |
| 4-3 | H | H | EtO | H | 4BrZ |
| 4-4 | H | H | PrO | H | 4BrZ |
| 4-5 | H | H | iPrO | H | 4BrZ |
| 4-6 | H | H | BuO | H | 4BrZ |
| 4-7 | H | H | iBuO | H | 4BrZ |
| 4-8 | H | H | sBuO | H | 4BrZ |
| 4-9 | H | H | tBuO | H | 4BrZ |
| 4-10 | H | H | BuO | H | 4BrZ |
| 4-11 | H | H | BzO | H | 4BrZ |
| 4-12 | H | MeO | Me | H | 4BrZ |
| 4-13 | H | MeO | Br | H | 4BrZ |
| 4-14 | H | EtO | F | H | 4BrZ |
| 4-15 | H | F | H | F | 4BrZ |
| 4-16 | H | H | F | H | 4BrZ |
| 4-17 | H | Cl | Me | H | 4BrZ |
| 4-18 | H | Cl | Et | H | 4BrZ |
| 4-19 | H | Et | H | H | 4BrZ |
| 4-20 | H | H | Br | H | 4BrZ |
| 4-21 | H | $CF_3$ | H | Br | 4BrZ |
| 4-22 | H | $CF_3$ | H | Cl | 4BrZ |
| 4-23 | H | H | H | $CF_3$ | 4BrZ |
| 4-24 | H | H | $CF_3$ | H | 4BrZ |
| 4-25 | H | Br | Me | Me | 4BrZ |
| 4-26 | H | F | Cl | H | 4BrZ |
| 4-27 | H | Br | H | Me | 4BrZ |

TABLE 4-continued

| Exp. Comp.No. | $R^{1a}$ | $R^{2a}$ | $R^{3a}$ | $R^{4a}$ | $R^{5a} = R^{6a}$ |
|---|---|---|---|---|---|
| 4-28 | H | H | tBu | H | 4BrZ |
| 4-29 | H | OH | H | H | 4BrZ |
| 4-30 | H | H | H | Me | 4BrZ |
| 4-31 | H | H | Cl | Cl | 4BrZ |
| 4-32 | H | F | F | F | 4BrZ |
| 4-33 | H | Br | BzO | H | 4BrZ |
| 4-34 | H | H | H | Cl | 4BrZ |
| 4-35 | H | Me | OH | Me | 4BrZ |
| 4-36 | H | MeO | H | H | 4BrZ |
| 4-37 | H | EtO | H | H | 4BrZ |
| 4-38 | H | PrO | H | H | 4BrZ |
| 4-39 | H | iPrO | H | H | 4BrZ |
| 4-40 | H | BuO | H | H | 4BrZ |
| 4-41 | H | iBuO | H | H | 4BrZ |
| 4-42 | H | sBuO | H | H | 4BrZ |
| 4-43 | H | tBuO | H | H | 4BrZ |
| 4-44 | H | BuO | H | H | 4BrZ |
| 4-45 | H | BzO | H | H | 4BrZ |
| 4-46 | H | Me | MeO | H | 4BrZ |
| 4-47 | H | Br | MeO | H | 4BrZ |
| 4-48 | H | F | EtO | H | 4BrZ |
| 4-49 | F | H | F | H | 4BrZ |
| 4-50 | H | F | H | H | 4BrZ |
| 4-51 | H | Me | Cl | H | 4BrZ |
| 4-52 | H | Et | Cl | H | 4BrZ |
| 4-53 | H | H | Et | H | 4BrZ |
| 4-54 | H | Br | H | H | 4BrZ |
| 4-55 | Br | H | $CF_3$ | H | 4BrZ |
| 4-56 | Cl | H | $CF_3$ | H | 4BrZ |
| 4-57 | $CF_3$ | H | H | H | 4BrZ |
| 4-58 | H | $CF_3$ | H | H | 4BrZ |
| 4-59 | Me | Me | Br | H | 4BrZ |
| 4-60 | H | Cl | F | H | 4BrZ |
| 4-61 | H | Br | H | Me | 4BrZ |
| 4-62 | H | tBu | H | H | 4BrZ |
| 4-63 | H | H | OH | H | 4BrZ |
| 4-64 | Me | H | H | H | 4BrZ |
| 4-65 | Cl | Cl | H | H | 4BrZ |
| 4-66 | F | F | F | H | 4BrZ |
| 4-67 | H | BzO | Br | H | 4BrZ |
| 4-68 | Cl | H | H | H | 4BrZ |
| 4-69 | Me | OH | Me | H | 4BrZ |
| 4-70 | Me | OH | Me | Me | 4BrZ |
| 4-71 | Me | OH | Me | Me | 4BrZ |
| 4-72 | Me | AcO | Me | Me | 4BrZ |

Preferable exemplification compounds in the tables are those having exemplification compound numbers 1-1, 1-2, 1-3, 1-4, 1-5, 1-6, 1-7, 1-8, 1-9, 1-1-10, 1-11, 1-36, 1-37, 1-38, 1-39, 1-40, 1-41, 1-42, 1-43, 1-44, 2-1, 2-2, 2-3, 2-4, 2-5, 2-6, 2-7, 2-8, 2-9, 2-10, 2-11, 2-36, 2-37, 2-38, 2-39, 2-40, 2-41, 2-42, 2-43, 2-44, 3-1, 3-2, 3-3, 3-4, 3-5, 3-6, 3-7, 3-8, 3-9, 3-10, 3-11, 3-36, 3-37, 3-38, 3-39, 3-40, 3-41, 3-42, 3-43, 3-44, 4-1, 4-2, 4-3, 4-4, 4-5, 4-6, 4-7, 4-8, 4-9, 4-10, 4-11, 4-36, 4-37, 4-38, 4-39, 4-40, 4-41, 4-42, 4-43 and 4-44; more preferably 1-1, 1-2, and 1-36; most preferably 1-2, which is N,N-di-tertiary butoxycarbonyl-2-nitro-5-methoxyaniline.

[2] A compound of formula (2) (which is referred to as compound (2) hereinafter) or a pharmaceutically acceptable salt thereof,

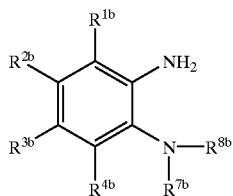

(2)

(wherein $R^{1b}$, $R^{2b}$, $R^{3b}$ and $R^{4b}$ are each independently hydrogen, hydroxyl, $C_1$–$C_6$ alkyl, $C_1$–$C_6$ alkoxy, benzyloxy, acetoxy, trifluoromethyl or halogen, $R^{7b}$ is $C_1$–$C_6$ alkyl and $R^{8b}$ is an amino protecting group).

Preferable compounds of formula (2) are:

[2-1] compounds and pharmaceutically acceptable salts thereof according to [2] wherein $R^{8b}$ is t-butoxycarbonyl, benzyloxycarbonyl, p-methoxybenzyloxycarbonyl or p-bromobenzyloxycarbonyl;

[2-2] compounds and pharmaceutically acceptable salts thereof according to [2] wherein $R^{8b}$ is t-butoxycarbonyl;

[2-3] compounds and pharmaceutically acceptable salts thereof according to any one of [2], [2-1] or [2-2] wherein $R^{7b}$ is $C_1$–$C_4$ alkyl;

[2-4] compounds and pharmaceutically acceptable salts thereof according to any one of [2], [2-1] or [2-2] wherein $R^{7b}$ is $C_1$–$C_2$ alkyl;

[2-5] compounds and pharmaceutically acceptable salts thereof according to any one of [2], [2-1] or [2-2] wherein $R^{7b}$ is methyl;

[2-6] compounds and pharmaceutically acceptable salts thereof according to any one of [2], [2-1], [2-2], [2-3], [2-4] or [2-5] wherein $R^{1b}$, $R^{2b}$, $R^{3b}$ and $R^{4b}$ are each independently hydrogen or $C_1$–$C_4$ alkoxy;

[2-7] compounds and pharmaceutically acceptable salts thereof according to any one of [2], [2-1], [2-2], [2-3], [2-4] or [2-5] wherein $R^{1b}$, $R^{2b}$, $R^{3b}$ and $R^{4b}$ are each independently hydrogen or methoxy; and

[2-8] compounds and pharmaceutically acceptable salts thereof according to [2] wherein $R^{1b}$, $R^{2b}$ and $R^{4b}$ are each hydrogen, $R^{3b}$ is methoxy, $R^{7b}$ is methyl and $R^{8b}$ is t-butoxycarbonyl.

The $C_1$–$C_6$ alkyl group of compound (2) is as defined in [1], preferably $C_1$–$C_4$ alkyl, more preferably methyl or ethyl and most preferably methyl.

The $C_1$–$C_6$ alkoxyl group of compound (2) is as defined in [1], preferably $C_1$–$C_4$ alkoxyl, more preferably methoxy or ethoxy and most preferably methoxy.

The halogen atom of compound (2) is as defined in [1], preferably fluorine, chlorine or bromine.

The amino protecting group of compound (2) is as defined in [1], preferably t-butoxycarbonyl, benzyl, p-methoxybenzyl, p-bromobenzyl, benzyloxycarbonyl, p-methoxybenzyloxycarbonyl or p-bromobenzyloxycarbonyl; more preferably t-butoxycarbonyl, benzyloxycarbonyl, p-methoxybenzyloxycarbonyl or p-bromobenzyloxycarbonyl; most preferably t-butoxycarbonyl.

In compound (2), preferably $R^{1b}$, $R^{2b}$, $R^{3b}$ and $R^{4b}$ are each independently hydrogen or $C_1$–$C_4$ alkoxy; more preferably $R^{1b}$, $R^{2b}$, $R^{3b}$ and $R^{4b}$ are each independently hydrogen or methoxy; most preferably $R^{1b}$, $R^{2b}$ and $R^{4b}$ are each hydrogen and most preferably $R^{3b}$ is methoxy, preferably $R^{7b}$ is $C_1$–$C_4$ alkyl; more preferably $C_1$–$C_2$ alkyl and most preferably methyl, and preferably $R^{8b}$ is t-butoxycarbonyl, benzyloxycarbonyl, p-methoxybenzyloxycarbonyl or p-bromobenzyloxycarbonyl; more preferably $R^{8b}$ is t-butoxycarbonyl.

Pharmaceutically acceptable salts of compound (2) are as defined in [1].

Typical compounds (2) are exemplified in Tables 5 to 8. Throughout the tables the following abbreviations are used with the following meaning:

Exp. Comp. No: Exemplification compound number

Me: methyl, Et: ethyl, Pr: propyl, iPr: isopropyl, Bu: butyl, iBu: isobutyl, sBu: secondary butyl, tBu: tertiary butyl, Bz: benzyl, Ac: acetyl, Boc: tertiary butoxycarbonyl, Z: benzyloxycarbonyl, Moz: p-methoxybenzyloxycarbonyl, 4BrZ: p-bromobenzyloxycarbonyl

TABLE 5

(2)

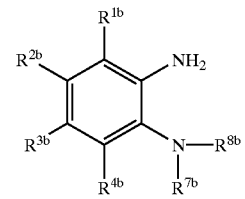

| Exp. Comp. No. | $R^{1b}$ | $R^{2b}$ | $R^{3b}$ | $R^{4b}$ | $R^{7b}$ | $R^{8b}$ |
|---|---|---|---|---|---|---|
| 5-2 | H | H | H | H | Me | Boc |
| 5-3 | H | H | H | H | Et | Boc |
| 5-4 | H | H | H | H | Pr | Boc |
| 5-5 | H | H | H | H | iPr | Boc |
| 5-6 | H | H | H | H | Bu | Boc |
| 5-8 | H | H | MeO | H | Me | Boc |
| 5-9 | H | H | MeO | H | Et | Boc |
| 5-10 | H | H | MeO | H | Pr | Boc |
| 5-11 | H | H | MeO | H | iPr | Boc |
| 5-12 | H | H | MeO | H | iBu | Boc |
| 5-13 | H | H | EtO | H | Me | Boc |
| 5-14 | H | H | PrO | H | Me | Boc |
| 5-15 | H | H | iPrO | H | Me | Boc |
| 5-16 | H | H | BuO | H | Me | Boc |
| 5-17 | H | H | iBuO | H | Me | Boc |
| 5-18 | H | H | sBuO | H | Me | Boc |
| 5-19 | H | H | tBuO | H | Me | Boc |
| 5-20 | H | H | BuO | H | Pr | Boc |
| 5-21 | H | H | BzO | H | Me | Boc |
| 5-22 | H | MeO | Me | H | Me | Boc |
| 5-23 | H | MeO | Br | H | Me | Boc |
| 5-24 | H | EtO | F | H | Me | Boc |
| 5-25 | H | F | H | F | Me | Boc |
| 5-26 | H | H | F | H | Me | Boc |
| 5-27 | H | Cl | Me | H | Me | Boc |
| 5-28 | H | Cl | Et | H | Et | Boc |
| 5-29 | H | Et | H | H | Me | Boc |
| 5-30 | H | H | Br | H | Me | Boc |
| 5-31 | H | $CF_3$ | H | Br | Me | Boc |
| 5-32 | H | $CF_3$ | H | Cl | Me | Boc |
| 5-33 | H | H | H | $CF_3$ | Me | Boc |
| 5-34 | H | H | $CF_3$ | H | Me | Boc |
| 5-35 | H | Br | Me | Me | Me | Boc |
| 5-36 | H | F | Cl | H | Me | Boc |
| 5-37 | H | Br | H | Me | Me | Boc |
| 5-38 | H | H | tBu | H | Me | Boc |
| 5-39 | H | OH | H | H | Me | Boc |
| 5-40 | H | H | H | Me | Me | Boc |
| 5-41 | H | H | Cl | Cl | Me | Boc |
| 5-42 | H | F | F | F | Me | Boc |
| 5-43 | H | Br | BzO | H | Me | Boc |
| 5-44 | H | H | H | Cl | Me | Boc |
| 5-45 | H | Me | OH | Me | Me | Boc |
| 5-46 | H | MeO | H | H | Me | Boc |
| 5-47 | H | MeO | H | H | Et | Boc |
| 5-48 | H | MeO | H | H | Pr | Boc |
| 5-49 | H | MeO | H | H | iPr | Boc |
| 5-50 | H | MeO | H | H | iBu | Boc |

TABLE 5-continued (2)

Structure: Benzene ring with $R^{1b}$, $R^{2b}$, $R^{3b}$, $R^{4b}$ substituents, $NH_2$ group, and $N(R^{7b})(R^{8b})$ group.

| Exp. Comp. No. | $R^{1b}$ | $R^{2b}$ | $R^{3b}$ | $R^{4b}$ | $R^{7b}$ | $R^{8b}$ |
|---|---|---|---|---|---|---|
| 5-51 | H | EtO | H | H | Me | Boc |
| 5-52 | H | PrO | H | H | Me | Boc |
| 5-53 | H | iPrO | H | H | Me | Boc |
| 5-54 | H | BuO | H | H | Me | Boc |
| 5-55 | H | iBuO | H | H | Me | Boc |
| 5-56 | H | sBuO | H | H | Me | Boc |
| 5-57 | H | tBuO | H | H | Me | Boc |
| 5-58 | H | BuO | H | H | Pr | Boc |
| 5-59 | H | BzO | H | H | Me | Boc |
| 5-60 | H | Me | MeO | H | Me | Boc |
| 5-61 | H | Br | MeO | H | Me | Boc |
| 5-62 | H | F | EtO | H | Me | Boc |
| 5-63 | F | H | F | H | Me | Boc |
| 5-64 | H | F | H | H | Me | Boc |
| 5-65 | H | Me | Cl | H | Me | Boc |
| 5-66 | H | Et | Cl | H | Et | Boc |
| 5-67 | H | H | Et | H | Me | Boc |
| 5-68 | H | Br | H | H | Me | Boc |
| 5-69 | Br | H | $CF_3$ | H | Me | Boc |
| 5-70 | Cl | H | $CF_3$ | H | Me | Boc |
| 5-71 | $CF_3$ | H | H | H | Me | Boc |
| 5-72 | H | $CF_3$ | H | H | Me | Boc |
| 5-73 | Me | Me | Br | H | Me | Boc |
| 5-74 | H | Cl | F | H | Me | Boc |
| 5-75 | H | Br | H | Me | Me | Boc |
| 5-76 | H | tBu | H | H | Me | Boc |
| 5-77 | H | H | OH | H | Me | Boc |
| 5-78 | Me | H | H | H | Me | Boc |
| 5-79 | Cl | Cl | H | H | Me | Boc |
| 5-80 | F | F | F | H | Me | Boc |
| 5-81 | H | BzO | Br | H | Me | Boc |
| 5-82 | Cl | H | H | H | Me | Boc |
| 5-83 | Me | OH | Me | H | Me | Boc |
| 5-84 | Me | OH | Me | Me | Me | Boc |
| 5-85 | Me | OH | Me | Me | Et | Boc |
| 5-86 | Me | AcO | Me | Me | Me | Boc |

TABLE 6

| Exp. Comp.No. | $R^{1b}$ | $R^{2b}$ | $R^{3b}$ | $R^{4b}$ | $R^{7b}$ | $R^{8b}$ |
|---|---|---|---|---|---|---|
| 6-2 | H | H | H | H | Me | Z |
| 6-3 | H | H | H | H | Et | Z |
| 6-4 | H | H | H | H | Pr | Z |
| 6-5 | H | H | H | H | iPr | Z |
| 6-6 | H | H | H | H | Bu | Z |
| 6-8 | H | H | MeO | H | Me | Z |
| 6-9 | H | H | MeO | H | Et | Z |
| 6-10 | H | H | MeO | H | Pr | Z |
| 6-11 | H | H | MeO | H | iPr | Z |
| 6-12 | H | H | MeO | H | iBu | Z |
| 6-13 | H | H | EtO | H | Me | Z |
| 6-14 | H | H | PrO | H | Me | Z |
| 6-15 | H | H | iPrO | H | Me | Z |
| 6-16 | H | H | BuO | H | Me | Z |
| 6-17 | H | H | iBuO | H | Me | Z |
| 6-18 | H | H | sBuO | H | Me | Z |
| 6-19 | H | H | tBuO | H | Me | Z |
| 6-20 | H | H | BuO | H | Pr | Z |
| 6-21 | H | H | BzO | H | Me | Z |
| 6-22 | H | MeO | Me | H | Me | Z |

TABLE 6-continued

| Exp. Comp.No. | $R^{1b}$ | $R^{2b}$ | $R^{3b}$ | $R^{4b}$ | $R^{7b}$ | $R^{8b}$ |
|---|---|---|---|---|---|---|
| 6-23 | H | MeO | Br | H | Me | Z |
| 6-24 | H | EtO | F | H | Me | Z |
| 6-25 | H | F | H | F | Me | Z |
| 6-26 | H | H | F | H | Me | Z |
| 6-27 | H | Cl | Me | H | Me | Z |
| 6-28 | H | Cl | Et | H | Et | Z |
| 6-29 | H | Et | H | H | Me | Z |
| 6-30 | H | H | Br | H | Me | Z |
| 6-31 | H | $CF_3$ | H | Br | Me | Z |
| 6-32 | H | $CF_3$ | H | Cl | Me | Z |
| 6-33 | H | H | H | $CF_3$ | Me | Z |
| 6-34 | H | H | $CF_3$ | H | Me | Z |
| 6-35 | H | Br | Me | Me | Me | Z |
| 6-36 | H | F | Cl | H | Me | Z |
| 6-37 | H | Br | H | Me | Me | Z |
| 6-38 | H | H | tBu | H | Me | Z |
| 6-39 | H | OH | H | H | Me | Z |
| 6-40 | H | H | H | Me | Me | Z |
| 6-41 | H | H | Cl | Cl | Me | Z |
| 6-42 | H | F | F | F | Me | Z |
| 6-43 | H | Br | BzO | H | Me | Z |
| 6-44 | H | H | H | Cl | Me | Z |
| 6-45 | H | Me | OH | Me | Me | Z |
| 6-46 | H | MeO | H | H | Me | Z |
| 6-47 | H | MeO | H | H | Et | Z |
| 6-48 | H | MeO | H | H | Pr | Z |
| 6-49 | H | MeO | H | H | iPr | Z |
| 6-50 | H | MeO | H | H | iBu | Z |
| 6-51 | H | EtO | H | H | Me | Z |
| 6-52 | H | PrO | H | H | Me | Z |
| 6-53 | H | iPrO | H | H | Me | Z |
| 6-54 | H | BuO | H | H | Me | Z |
| 6-55 | H | iBuO | H | H | Me | Z |
| 6-56 | H | sBuO | H | H | Me | Z |
| 6-57 | H | tBuO | H | H | Me | Z |
| 6-58 | H | BuO | H | H | Pr | Z |
| 6-59 | H | BzO | H | H | Me | Z |
| 6-60 | H | Me | MeO | H | Me | Z |
| 6-61 | H | Br | MeO | H | Me | Z |
| 6-62 | H | F | EtO | H | Me | Z |
| 6-63 | F | H | F | H | Me | Z |
| 6-64 | H | F | H | H | Me | Z |
| 6-65 | H | Me | Cl | H | Me | Z |
| 6-66 | H | Et | Cl | H | Et | Z |
| 6-67 | H | H | Et | H | Me | Z |
| 6-68 | H | Br | H | H | Me | Z |
| 6-69 | Br | H | $CF_3$ | H | Me | Z |
| 6-70 | Cl | H | $CF_3$ | H | Me | Z |
| 6-71 | $CF_3$ | H | H | H | Me | Z |
| 6-72 | H | $CF_3$ | H | H | Me | Z |
| 6-73 | Me | Me | Br | H | Me | Z |
| 6-74 | H | Cl | F | H | Me | Z |
| 6-75 | H | Br | H | Me | Me | Z |
| 6-76 | H | tBu | H | H | Me | Z |
| 6-77 | H | H | OH | H | Me | Z |
| 6-78 | Me | H | H | H | Me | Z |
| 6-79 | Cl | Cl | H | H | Me | Z |
| 6-80 | F | F | F | H | Me | Z |
| 6-81 | H | BzO | Br | H | Me | Z |
| 6-82 | Cl | H | H | H | Me | Z |
| 6-83 | Me | OH | Me | H | Me | Z |
| 6-84 | Me | OH | Me | Me | Me | Z |
| 6-85 | Me | OH | Me | Me | Et | Z |
| 6-86 | Me | AcO | Me | Me | Me | Z |

TABLE 7

| Exp. Comp.No | $R^{1b}$ | $R^{2b}$ | $R^{3b}$ | $R^{4b}$ | $R^{7b}$ | $R^{8b}$ |
|---|---|---|---|---|---|---|
| 7-2 | H | H | H | H | Me | Moz |
| 7-3 | H | H | H | H | Et | Moz |
| 7-4 | H | H | H | H | Pr | Moz |

TABLE 7-continued

| Exp. Comp.No | $R^{1b}$ | $R^{2b}$ | $R^{3b}$ | $R^{4b}$ | $R^{7b}$ | $R^{8b}$ |
|---|---|---|---|---|---|---|
| 7-5 | H | H | H | H | iPr | Moz |
| 7-6 | H | H | H | H | Bu | Moz |
| 7-8 | H | H | MeO | H | Me | Moz |
| 7-9 | H | H | MeO | H | Et | Moz |
| 7-10 | H | H | MeO | H | Pr | Moz |
| 7-11 | H | H | MeO | H | iPr | Moz |
| 7-12 | H | H | MeO | H | iBu | Moz |
| 7-13 | H | H | EtO | H | Me | Moz |
| 7-14 | H | H | PrO | H | Me | Moz |
| 7-15 | H | H | iPrO | H | Me | Moz |
| 7-16 | H | H | BuO | H | Me | Moz |
| 7-17 | H | H | iBuO | H | Me | Moz |
| 7-18 | H | H | sBuO | H | Me | Moz |
| 7-19 | H | H | tBuO | H | Me | Moz |
| 7-20 | H | H | BuO | H | Pr | Moz |
| 7-21 | H | H | BzO | H | Me | Moz |
| 7-22 | H | MeO | Me | H | Me | Moz |
| 7-23 | H | MeO | Br | H | Me | Moz |
| 7-24 | H | EtO | F | H | Me | Moz |
| 7-25 | H | F | H | F | Me | Moz |
| 7-26 | H | H | F | H | Me | Moz |
| 7-27 | H | Cl | Me | H | Me | Moz |
| 7-28 | H | Cl | Et | H | Et | Moz |
| 7-29 | H | Et | H | H | Me | Moz |
| 7-30 | H | H | Br | H | Me | Moz |
| 7-31 | H | $CF_3$ | H | Br | Me | Moz |
| 7-32 | H | $CF_3$ | H | Cl | Me | Moz |
| 7-33 | H | H | H | $CF_3$ | Me | Moz |
| 7-34 | H | H | $CF_3$ | H | Me | Moz |
| 7-35 | H | Br | Me | Me | Me | Moz |
| 7-36 | H | F | Cl | H | Me | Moz |
| 7-37 | H | Br | H | Me | Me | Moz |
| 7-38 | H | H | tBu | H | Me | Moz |
| 7-39 | H | OH | H | H | Me | Moz |
| 7-40 | H | H | H | Me | Me | Moz |
| 7-41 | H | H | Cl | Cl | Me | Moz |
| 7-42 | H | F | F | F | Me | Moz |
| 7-43 | H | Br | BzO | H | Me | Moz |
| 7-44 | H | H | H | Cl | Me | Moz |
| 7-45 | H | Me | OH | Me | Me | Moz |
| 7-46 | H | MeO | H | H | Me | Moz |
| 7-47 | H | MeO | H | H | Et | Moz |
| 7-48 | H | MeO | H | H | Pr | Moz |
| 7-49 | H | MeO | H | H | iPr | Moz |
| 7-50 | H | MeO | H | H | iBu | Moz |
| 7-51 | H | EtO | H | H | Me | Moz |
| 7-52 | H | PrO | H | H | Me | Moz |
| 7-53 | H | iPrO | H | H | Me | Moz |
| 7-54 | H | BuO | H | H | Me | Moz |
| 7-55 | H | iBuO | H | H | Me | Moz |
| 7-56 | H | sBuO | H | H | Me | Moz |
| 7-57 | H | tBuO | H | H | Me | Moz |
| 7-58 | H | BuO | H | H | Pr | Moz |
| 7-59 | H | BzO | H | H | Me | Moz |
| 7-60 | H | Me | MeO | H | Me | Moz |
| 7-61 | H | Br | MeO | H | Me | Moz |
| 7-62 | H | F | EtO | H | Me | Moz |
| 7-63 | F | H | F | H | Me | Moz |
| 7-64 | H | F | H | H | Me | Moz |
| 7-65 | H | Me | Cl | H | Me | Moz |
| 7-66 | H | Et | Cl | H | Et | Moz |
| 7-67 | H | H | Et | H | Me | Moz |
| 7-68 | H | Br | H | H | Me | Moz |
| 7-69 | Br | H | $CF_3$ | H | Me | Moz |
| 7-70 | Cl | H | $CF_3$ | H | Me | Moz |
| 7-71 | $CF_3$ | H | H | H | Me | Moz |
| 7-72 | H | $CF_3$ | H | H | Me | Moz |
| 7-73 | Me | Me | Br | H | Me | Moz |
| 7-74 | H | Cl | F | H | Me | Moz |
| 7-75 | H | Br | H | Me | Me | Moz |
| 7-76 | H | tBu | H | H | Me | Moz |
| 7-77 | H | H | OH | H | Me | Moz |
| 7-78 | Me | H | H | H | Me | Moz |
| 7-79 | Cl | Cl | H | H | Me | Moz |
| 7-80 | F | F | H | H | Me | Moz |
| 7-81 | H | BzO | Br | H | Me | Moz |
| 7-82 | Cl | H | H | H | Me | Moz |
| 7-83 | Me | OH | Me | H | Me | Moz |
| 7-84 | Me | OH | Me | Me | Me | Moz |
| 7-85 | Me | OH | Me | Me | Et | Moz |
| 7-86 | Me | AcO | Me | Me | Me | Moz |

TABLE 8

| Exp. Comp.No. | $R^{1b}$ | $R^{2b}$ | $R^{3b}$ | $R^{4b}$ | $R^{7b}$ | $R^{8b}$ |
|---|---|---|---|---|---|---|
| 8-2 | H | H | H | H | Me | 4BrZ |
| 8-3 | H | H | H | H | Et | 4BrZ |
| 8-4 | H | H | H | H | Pr | 4BrZ |
| 8-5 | H | H | H | H | iPr | 4BrZ |
| 8-6 | H | H | H | H | Bu | 4BrZ |
| 8-8 | H | H | MeO | H | Me | 4BrZ |
| 8-9 | H | H | MeO | H | Et | 4BrZ |
| 8-10 | H | H | MeO | H | Pr | 4BrZ |
| 8-11 | H | H | MeO | H | iPr | 4BrZ |
| 8-12 | H | H | MeO | H | iBu | 4BrZ |
| 8-13 | H | H | EtO | H | Me | 4BrZ |
| 8-14 | H | H | Pro | H | Me | 4BrZ |
| 8-15 | H | H | iPrO | H | Me | 4BrZ |
| 8-16 | H | H | BuO | H | Me | 4BrZ |
| 8-17 | H | H | iBuO | H | Me | 4BrZ |
| 8-18 | H | H | sBuO | H | Me | 4BrZ |
| 8-19 | H | H | tBuO | H | Me | 4BrZ |
| 8-20 | H | H | BuO | H | Pr | 4BrZ |
| 8-21 | H | H | BzO | H | Me | 4BrZ |
| 8-22 | H | MeO | Me | H | Me | 4BrZ |
| 8-23 | H | MeO | Br | H | Me | 4BrZ |
| 8-24 | H | EtO | F | H | Me | 4BrZ |
| 8-25 | H | F | H | F | Me | 4BrZ |
| 8-26 | H | H | F | H | Me | 4BrZ |
| 8-27 | H | Cl | Me | H | Me | 4BrZ |
| 8-28 | H | Cl | Et | H | Et | 4BrZ |
| 8-29 | H | Et | H | H | Me | 4BrZ |
| 8-30 | H | H | Br | H | Me | 4BrZ |
| 8-31 | H | $CF_3$ | H | Br | Me | 4BrZ |
| 8-32 | H | $CF_3$ | H | Cl | Me | 4BrZ |
| 8-33 | H | H | H | $CF_3$ | Me | 4BrZ |
| 8-34 | H | H | $CF_3$ | H | Me | 4BrZ |
| 8-35 | H | Br | Me | Me | Me | 4BrZ |
| 8-36 | H | F | Cl | H | Me | 4BrZ |
| 8-37 | H | Br | H | Me | Me | 4BrZ |
| 8-38 | H | H | tBu | H | Me | 4BrZ |
| 8-39 | H | OH | H | H | Me | 4BrZ |
| 8-40 | H | H | H | Me | Me | 4BrZ |
| 8-41 | H | H | Cl | Cl | Me | 4BrZ |
| 8-42 | H | F | F | F | Me | 4BrZ |
| 8-43 | H | Br | BzO | H | Me | 4BrZ |
| 8-44 | H | H | H | Cl | Me | 4BrZ |
| 8-45 | H | Me | OH | Me | Me | 4BrZ |
| 8-46 | H | MeO | H | H | Me | 4BrZ |
| 8-47 | H | MeO | H | H | Et | 4BrZ |
| 8-48 | H | MeO | H | H | Pr | 4BrZ |
| 8-49 | H | MeO | H | H | iPr | 4BrZ |
| 8-50 | H | MeO | H | H | iBu | 4BrZ |
| 8-51 | H | EtO | H | H | Me | 4BrZ |
| 8-52 | H | Pro | H | H | Me | 4BrZ |
| 8-53 | H | iPrO | H | H | Me | 4BrZ |
| 8-54 | H | BuO | H | H | Me | 4BrZ |
| 8-55 | H | iBuO | H | H | Me | 4BrZ |
| 8-56 | H | sBuO | H | H | Me | 4BrZ |
| 8-57 | H | tBuO | H | H | Me | 4BrZ |
| 8-58 | H | BuO | H | H | Pr | 4BrZ |
| 8-59 | H | BzO | H | H | Me | 4BrZ |
| 8-60 | H | Me | MeO | H | Me | 4BrZ |
| 8-61 | H | Br | MeO | H | Me | 4BrZ |
| 8-62 | H | F | EtO | H | Me | 4BrZ |
| 8-63 | F | H | F | H | Me | 4BrZ |
| 8-64 | H | F | H | H | Me | 4BrZ |

TABLE 8-continued

| Exp. Comp.No. | $R^{1b}$ | $R^{2b}$ | $R^{3b}$ | $R^{4b}$ | $R^{7b}$ | $R^{8b}$ |
|---|---|---|---|---|---|---|
| 8-65 | H | Me | Cl | H | Me | 4BrZ |
| 8-66 | H | Et | Cl | H | Et | 4BrZ |
| 8-67 | H | H | Et | H | Me | 4BrZ |
| 8-68 | H | Br | H | H | Me | 4BrZ |
| 8-69 | Br | H | $CF_3$ | H | Me | 4BrZ |
| 8-70 | Cl | H | $CF_3$ | H | Me | 4BrZ |
| 8-71 | $CF_3$ | H | H | H | Me | 4BrZ |
| 8-72 | H | $CF_3$ | H | H | Me | 4BrZ |
| 8-73 | Me | Me | Br | H | Me | 4BrZ |
| 8-74 | H | Cl | F | H | Me | 4BrZ |
| 8-75 | H | Br | H | Me | Me | 4BrZ |
| 8-76 | H | tBu | H | H | Me | 4BrZ |
| 8-77 | H | H | OH | H | Me | 4BrZ |
| 8-78 | Me | H | H | H | Me | 4BrZ |
| 8-79 | Cl | Cl | H | H | Me | 4BrZ |
| 8-80 | F | F | F | H | Me | 4BrZ |
| 8-81 | H | BzO | Br | H | Me | 4BrZ |
| 8-82 | Cl | H | H | H | Me | 4BrZ |
| 8-83 | Me | OH | Me | H | Me | 4BrZ |
| 8-84 | Me | OH | Me | Me | Me | 4BrZ |
| 8-85 | Me | OH | Me | Me | Et | 4BrZ |
| 8-86 | Me | AcO | Me | Me | Me | 4BrZ |

Preferable exemplification compounds in the tables are those having exemplification compound numbers 5-2, 5-3, 5-4, 5-5, 5-6, 5-8, 5-9, 5-10, 5-11, 5-12, 5-13, 5-14, 5-15, 5-16, 5-17, 5-18, 5-19, 5-20, 5-46, 5-47, 5-48, 5-49, 5-50, 5-51, 5-52, 5-53, 5-54, 5-55, 5-56, 5-57, 5-58, 6-2, 6-3, 6-4, 6-5, 6-6, 6-8, 6-9, 6-10, 6-11, 6-12, 6-13, 6-14, 6-15, 6-16, 6-17, 6-18, 6-19, 6-20, 6-46, 6-47, 6-48, 6-49, 6-50, 6-51, 6-52, 6-53, 6-54, 6-55, 6-56, 6-57, 6-58, 7-2, 7-3, 7-4, 7-5, 7-6, 7-8, 7-9, 7-10, 7-11, 7-12, 7-13, 7-14, 7-15, 7-16, 7-17, 7-18, 7-19, 7-20, 7-46, 7-47, 7-48, 7-49, 7-50, 7-51, 7-52, 7-53, 7-54, 7-55, 7-56, 7-57, 7-58, 8-2, 8-3, 8-4, 8-5, 8-6, 8-8, 8-9, 8-10, 8-11, 8-12, 8-13, 8-14, 8-15, 8-16, 8-17, 8-18, 8-19, 8-20, 8-46, 8-47, 8-48, 8-49, 8-50, 8-51, 8-52, 8-53, 8-54, 8-55, 8-56, 8-57 and 8-58; more preferably 5-8, 5-9, 5-49 and 5-47; most preferably 5-8, which is N-methyl-N-tert-butoxycarbonyl-2-amino-5-methoxyaniline.

[3] A compound of formula (3) (which is referred to as compound (3) hereinafter) or a pharmaceutically acceptable salt thereof,

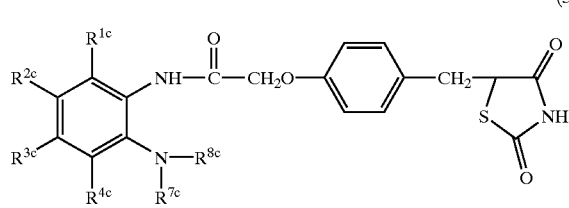

(3)

(wherein $R^{1c}$, $R^{2c}$, $R^{3c}$ and $R^{4c}$ are each independently hydrogen, hydroxyl, $C_1$–$C_6$ alkyl, $C_1$–$C_6$ alkoxy, benzyloxy, acetoxy, trifluoromethyl or halogen, $R^{7c}$ is $C_1$–$C_6$ alkyl and $R^{8c}$ is hydrogen or an amino protecting group).

Preferable compounds (3) are:

[3-1] compounds and pharmaceutically acceptable salts thereof according to [3] wherein $R^{8c}$ is hydrogen, t-butoxycarbonyl, benzyloxycarbonyl, p-methoxybenzyloxycarbonyl or p-bromobenzyloxycarbonyl;

[3-2] compounds and pharmaceutically acceptable salts thereof according to [3] wherein $R^{8c}$ is hydrogen or t-butoxycarbonyl;

[3-3] compounds and pharmaceutically acceptable salts thereof according to [3] wherein $R^{8c}$ is t-butoxycarbonyl;

[3-4] compounds and pharmaceutically acceptable salts thereof according to any one of [3], [3-1], [3-2] or [3-3] wherein $R^{7c}$ is $C_1$–$C_4$ alkyl;

[3-5] compounds and pharmaceutically acceptable salts thereof according to any one of [3], [3-1], [3-2] or [3-3] wherein $R^{7c}$ is $C_1$–$C_2$ alkyl;

[3-6] compounds and pharmaceutically acceptable salts thereof according to any one of [3], [3-1], [3-2] or [3-3] wherein $R^{7c}$ is methyl;

[3-7] compounds and pharmaceutically acceptable salts thereof according to any one of [3], [3-1], [3-2], [3-3], [3-4], [3-5] or [3-6] wherein $R^{1c}$, $R^{2c}$, $R^{3c}$ and $R^{4c}$ are each independently hydrogen or $C_1$–$C_4$ alkoxy;

[3-8] compounds and pharmaceutically acceptable salts thereof according to any one of [3], [3-1], [3-2], [3-3], [3-4], [3-5] or [3-6] wherein $R^{1c}$, $R^{2c}$, $R^{3c}$ and $R^{4c}$ are each independently hydrogen or methoxy; and

[3-9] compounds and pharmaceutically acceptable salts thereof according to [3] wherein $R^{1c}$, $R^{2c}$ and $R^{4c}$ are each hydrogen, $R^{3c}$ is methoxy, $R^{7c}$ is methyl and $R^{8c}$ is t-butoxycarbonyl.

The $C_1$–$C_6$ alkyl group of compound (3) is as defined in [1]; preferably $C_1$–$C_4$ alkyl; more preferably methyl or ethyl and most preferably methyl.

The $C_1$–$C_6$ alkoxyl group of compound (3) is as defined in [1]; preferably $C_1$–$C_4$ alkoxy; more preferably methoxy or ethoxy and most preferably methoxy.

The halogen atom of compound (3) is as defined in [1], preferably fluorine, chlorine or bromine.

The amino protecting group of compound (3) is as defined in [1], preferably t-butoxycarbonyl, benzyl, p-methoxybenzyl, p-bromobenzyl, benzyloxycarbonyl, p-methoxybenzyloxycarbonyl or p-bromobenzyloxycarbonyl; more preferably t-butoxycarbonyl, benzyloxycarbonyl, p-methoxybenzyloxycarbonyl or p-bromobenzyloxycarbonyl; most preferably t-butoxycarbonyl.

In compound (3), preferably $R^{1c}$, $R^{2c}$, $R^{3c}$ and $R^{4c}$ are each independently hydrogen or $C_1$–$C_4$ alkoxy; more preferably $R^{1c}$, $R^{2c}$, $R^{3c}$ and $R^{4c}$ are each independently hydrogen or methoxy; most preferably $R^{1c}$ $R^{2c}$ and $R^{4c}$ are each hydrogen and most preferably $R^{3c}$ is methoxy; and preferably $R^{7c}$ is $C_1$–$C_4$ alkyl; more preferably $C_1$–$C_2$ alkyl and most preferably methyl.

preferably $R^{8c}$ is hydrogen, t-butoxycarbonyl, benzyloxycarbonyl, p-methoxybenzyloxycarbonyl or p-bromobenzyloxycarbonyl; more preferably $R^{8c}$ is hydrogen or t-butoxycarbonyl; most preferably $R^{8c}$ is t-butoxycarbonyl.

Pharmaceutically acceptable salts of the compound (3) are as defined in [1]. Typical compounds (3) are exemplified in Tables 9 to 13. Throughout the tables the following abbreviations are used with the following meaning:

Exp. Comp. No: Exemplification compound number

Me: methyl, Et: ethyl, Pr: propyl, iPr: isopropyl, Bu: butyl, iBu: isobutyl, sBu: secondary butyl, tBu: tertiary butyl, Bz: benzyl, Ac: acetyl, Boc: tertiary butoxycarbonyl, Z: benzyloxycarbonyl, Moz: p-methoxybenzyloxycarbonyl, 4BrZ: p-bromobenzyloxycarbonyl

TABLE 9

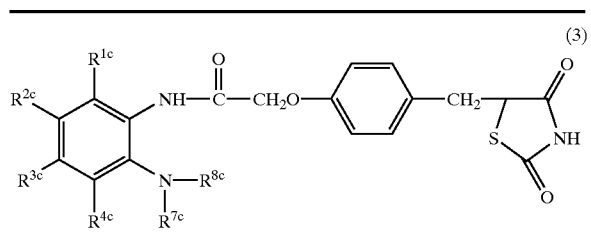

| Exp. Comp. No. | R¹ᶜ | R²ᶜ | R³ᶜ | R⁴ᶜ | R⁷ᶜ | R⁸ᶜ |
|---|---|---|---|---|---|---|
| 9-2 | H | H | H | H | Me | Boc |
| 9-3 | H | H | H | H | Et | Boc |
| 9-4 | H | H | H | H | Pr | Boc |
| 9-5 | H | H | H | H | iPr | Boc |
| 9-6 | H | H | H | H | Bu | Boc |
| 9-8 | H | H | MeO | H | Me | Boc |
| 9-9 | H | H | MeO | H | Et | Boc |
| 9-10 | H | H | MeO | H | Pr | Boc |
| 9-11 | H | H | MeO | H | iPr | Boc |
| 9-12 | H | H | MeO | H | iBu | Boc |
| 9-13 | H | H | EtO | H | Me | Boc |
| 9-14 | H | H | PrO | H | Me | Boc |
| 9-15 | H | H | iPrO | H | Me | Boc |
| 9-16 | H | H | BuO | H | Me | Boc |
| 9-17 | H | H | iBuO | H | Me | Boc |
| 9-18 | H | H | sBuO | H | Me | Boc |
| 9-19 | H | H | tBuO | H | Me | Boc |
| 9-20 | H | H | BuO | H | Pr | Boc |
| 9-21 | H | H | BzO | H | Me | Boc |
| 9-22 | H | MeO | Me | H | Me | Boc |
| 9-23 | H | MeO | Br | H | Me | Boc |
| 9-24 | H | EtO | F | H | Me | Boc |
| 9-25 | H | F | H | F | Me | Boc |
| 9-26 | H | H | F | H | Me | Boc |
| 9-27 | H | Cl | Me | H | Me | Boc |
| 9-28 | H | Cl | Et | H | Et | Boc |
| 9-29 | H | Et | H | H | Me | Boc |
| 9-30 | H | H | Br | H | Me | Boc |
| 9-31 | H | CF₃ | H | Br | Me | Boc |
| 9-32 | H | CF₃ | H | Cl | Me | Boc |
| 9-33 | H | H | H | CF₃ | Me | Boc |
| 9-34 | H | H | CF₃ | H | Me | Boc |
| 9-35 | H | Br | Me | Me | Me | Boc |
| 9-36 | H | F | Cl | H | Me | Boc |
| 9-37 | H | Br | H | Me | Me | Boc |
| 9-38 | H | H | tBu | H | Me | Boc |
| 9-39 | H | OH | H | H | Me | Boc |
| 9-40 | H | H | H | Me | Me | Boc |
| 9-41 | H | H | Cl | Cl | Me | Boc |
| 9-42 | H | F | F | F | Me | Boc |
| 9-43 | H | Br | BzO | H | Me | Boc |
| 9-44 | H | H | H | Cl | Me | Boc |
| 9-45 | H | Me | OH | Me | Me | Boc |
| 9-46 | H | MeO | H | H | Me | Boc |
| 9-47 | H | MeO | H | H | Et | Boc |
| 9-48 | H | MeO | H | H | Pr | Boc |
| 9-49 | H | MeO | H | H | iPr | Boc |
| 9-50 | H | MeO | H | H | iBu | Boc |
| 9-51 | H | EtO | H | H | Me | Boc |
| 9-52 | H | PrO | H | H | Me | Boc |
| 9-53 | H | iPrO | H | H | Me | Boc |
| 9-54 | H | BuO | H | H | Me | Boc |
| 9-55 | H | iBuO | H | H | Me | Boc |
| 9-56 | H | sBuO | H | H | Me | Boc |
| 9-57 | H | tBuO | H | H | Me | Boc |
| 9-58 | H | BuO | H | H | Pr | Boc |
| 9-59 | H | BzO | H | H | Me | Boc |
| 9-60 | H | Me | MeO | H | Me | Boc |
| 9-61 | H | Br | MeO | H | Me | Boc |
| 9-62 | H | F | EtO | H | Me | Boc |
| 9-63 | F | H | F | H | Me | Boc |
| 9-64 | H | F | H | H | Me | Boc |
| 9-65 | H | Me | Cl | H | Me | Boc |
| 9-66 | H | Et | Cl | H | Et | Boc |
| 9-67 | H | H | Et | H | Me | Boc |

TABLE 9-continued

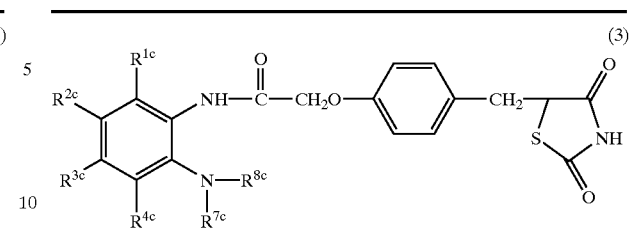

| Exp. Comp. No. | R¹ᶜ | R²ᶜ | R³ᶜ | R⁴ᶜ | R⁷ᶜ | R⁸ᶜ |
|---|---|---|---|---|---|---|
| 9-68 | H | Br | H | H | Me | Boc |
| 9-69 | Br | H | CF₃ | H | Me | Boc |
| 9-70 | Cl | H | CF₃ | H | Me | Boc |
| 9-71 | CF₃ | H | H | H | Me | Boc |
| 9-72 | H | CF₃ | H | H | Me | Boc |
| 9-73 | Me | Me | Br | H | Me | Boc |
| 9-74 | H | Cl | F | H | Me | Boc |
| 9-75 | H | Br | H | Me | Me | Boc |
| 9-76 | H | tBu | H | H | Me | Boc |
| 9-77 | H | H | OH | H | Me | Boc |
| 9-78 | Me | H | H | H | Me | Boc |
| 9-79 | Cl | Cl | H | H | Me | Boc |
| 9-80 | F | F | F | H | Me | Boc |
| 9-81 | H | BzO | Br | H | Me | Boc |
| 9-82 | Cl | H | H | H | Me | Boc |
| 9-83 | Me | OH | Me | H | Me | Boc |
| 9-84 | Me | OH | Me | Me | Me | Boc |
| 9-85 | Me | OH | Me | Me | Et | Boc |
| 9-86 | Me | AcO | Me | Me | Me | Boc |

TABLE 10

| Exp. Comp.No. | R¹ᶜ | R²ᶜ | R³ᶜ | R⁴ᶜ | R⁷ᶜ | R⁸ᶜ |
|---|---|---|---|---|---|---|
| 10-2 | H | H | H | H | Me | Z |
| 10-3 | H | H | H | H | Et | Z |
| 10-4 | H | H | H | H | Pr | Z |
| 10-5 | H | H | H | H | iPr | Z |
| 10-6 | H | H | H | H | Bu | Z |
| 10-8 | H | H | MeO | H | Me | Z |
| 10-9 | H | H | MeO | H | Et | Z |
| 10-10 | H | H | MeO | H | Pr | Z |
| 10-11 | H | H | MeO | H | iPr | Z |
| 10-12 | H | H | MeO | H | iBu | Z |
| 10-13 | H | H | EtO | H | Me | Z |
| 10-14 | H | H | PrO | H | Me | Z |
| 10-15 | H | H | iPrO | H | Me | Z |
| 10-16 | H | H | BuO | H | Me | Z |
| 10-17 | H | H | iBuO | H | Me | Z |
| 10-18 | H | H | sBuO | H | Me | Z |
| 10-19 | H | H | tBuO | H | Me | Z |
| 10-20 | H | H | BuO | H | Pr | Z |
| 10-21 | H | H | BzO | H | Me | Z |
| 10-22 | H | MeO | Me | H | Me | Z |
| 10-23 | H | MeO | Br | H | Me | Z |
| 10-24 | H | EtO | F | H | Me | Z |
| 10-25 | H | F | H | F | Me | Z |
| 10-26 | H | H | F | H | Me | Z |
| 10-27 | H | Cl | Me | H | Me | Z |
| 10-28 | H | Cl | Et | H | Et | Z |
| 10-29 | H | Et | H | H | Me | Z |
| 10-30 | H | H | Br | H | Me | Z |
| 10-31 | H | CF₃ | H | Br | Me | Z |
| 10-32 | H | CF₃ | H | Cl | Me | Z |
| 10-33 | H | H | H | CF₃ | Me | Z |
| 10-34 | H | H | CF₃ | H | Me | Z |
| 10-35 | H | Br | Me | Me | Me | Z |
| 10-36 | H | F | Cl | H | Me | Z |
| 10-37 | H | Br | H | Me | Me | Z |
| 10-38 | H | H | tBu | H | Me | Z |
| 10-39 | H | OH | H | H | Me | Z |

TABLE 10-continued

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 10-40 | H | H | H | Me | Me | Z |
| 10-41 | H | H | Cl | Cl | Me | Z |
| 10-42 | H | F | F | F | Me | Z |
| 10-43 | H | Br | BzO | H | Me | Z |
| 10-44 | H | H | H | Cl | Me | Z |
| 10-45 | H | Me | OH | Me | Me | Z |
| 10-46 | H | MeO | H | H | Me | Z |
| 10-47 | H | MeO | H | H | Et | Z |
| 10-48 | H | MeO | H | H | Pr | Z |
| 10-49 | H | MeO | H | H | iPr | Z |
| 10-50 | H | MeO | H | H | iBu | Z |
| 10-51 | H | EtO | H | H | Me | Z |
| 10-52 | H | PrO | H | H | Me | Z |
| 10-53 | H | iPrO | H | H | Me | Z |
| 10-54 | H | BuO | H | H | Me | Z |
| 10-55 | H | iBuO | H | H | Me | Z |
| 10-56 | H | sBuO | H | H | Me | Z |
| 10-57 | H | tBuO | H | H | Me | Z |
| 10-58 | H | BuO | H | H | Pr | Z |
| 10-59 | H | BzO | H | H | Me | Z |
| 10-60 | H | Me | MeO | H | Me | Z |
| 10-61 | H | Br | MeO | H | Me | Z |
| 10-62 | H | F | EtO | H | Me | Z |
| 10-63 | F | H | F | H | Me | Z |
| 10-64 | H | F | H | H | Me | Z |
| 10-65 | H | Me | Cl | H | Me | Z |
| 10-66 | H | Et | Cl | H | Et | Z |
| 10-67 | H | H | Et | H | Me | Z |
| 10-68 | H | Br | H | H | Me | Z |
| 10-69 | Br | H | $CF_3$ | H | Me | Z |
| 10-70 | Cl | H | $CF_3$ | H | Me | Z |
| 10-71 | $CF_3$ | H | H | H | Me | Z |
| 10-72 | H | $CF_3$ | H | H | Me | Z |
| 10-73 | Me | Me | Br | H | Me | Z |
| 10-74 | H | Cl | F | H | Me | Z |
| 10-75 | H | Br | H | Me | Me | Z |
| 10-76 | H | tBu | H | H | Me | Z |
| 10-77 | H | H | OH | H | Me | Z |
| 10-78 | Me | H | H | H | Me | Z |
| 10-79 | Cl | Cl | H | H | Me | Z |
| 10-80 | F | F | F | H | Me | Z |
| 10-81 | H | BzO | Br | H | Me | Z |
| 10-82 | Cl | H | H | H | Me | Z |
| 10-83 | Me | OH | Me | H | Me | Z |
| 10-84 | Me | OH | Me | Me | Me | Z |
| 10-85 | Me | OH | Me | Me | Et | Z |
| 10-86 | Me | AcO | Me | Me | Me | Z |

TABLE 11

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 11-2 | H | H | H | H | Me | Moz |
| 11-3 | H | H | H | H | Et | Moz |
| 11-4 | H | H | H | H | Pr | Moz |
| 11-5 | H | H | H | H | iPr | Moz |
| 11-6 | H | H | H | H | Bu | Moz |
| 11-8 | H | H | MeO | H | Me | Moz |
| 11-9 | H | H | MeO | H | Et | Moz |
| 11-10 | H | H | MeO | H | Pr | Moz |
| 11-11 | H | H | MeO | H | iPr | Moz |
| 11-12 | H | H | MeO | H | iBu | Moz |
| 11-13 | H | H | EtO | H | Me | Moz |
| 11-14 | H | H | Pro | H | Me | Moz |
| 11-15 | H | H | iPrO | H | Me | Moz |
| 11-16 | H | H | BuO | H | Me | Moz |
| 11-17 | H | H | iBuO | H | Me | Moz |
| 11-18 | H | H | sBuO | H | Me | Moz |
| 11-19 | H | H | tBuO | H | Me | Moz |
| 11-20 | H | H | BuO | H | Pr | Moz |
| 11-21 | H | H | BzO | H | Me | Moz |
| 11-22 | H | MeO | Me | H | Me | Moz |

TABLE 11-continued

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 11-23 | H | MeO | Br | H | Me | Moz |
| 11-24 | H | EtO | F | H | Me | Moz |
| 11-25 | H | F | H | F | Me | Moz |
| 11-26 | H | H | F | H | Me | Moz |
| 11-27 | H | Cl | Me | H | Me | Moz |
| 11-28 | H | Cl | Et | H | Et | Moz |
| 11-29 | H | Et | H | H | Me | Moz |
| 11-30 | H | H | Br | H | Me | Moz |
| 11-31 | H | $CF_3$ | H | Br | Me | Moz |
| 11-32 | H | $CF_3$ | H | Cl | Me | Moz |
| 11-33 | H | H | H | $CF_3$ | Me | Moz |
| 11-34 | H | H | $CF_3$ | H | Me | Moz |
| 11-35 | H | Br | Me | Me | Me | Moz |
| 11-36 | H | F | Cl | H | Me | Moz |
| 11-37 | H | Br | H | Me | Me | Moz |
| 11-38 | H | H | tBu | H | Me | Moz |
| 11-39 | H | OH | H | H | Me | Moz |
| 11-40 | H | H | H | Me | Me | Moz |
| 11-41 | H | H | Cl | Cl | Me | Moz |
| 11-42 | H | F | F | F | Me | Moz |
| 11-43 | H | Br | BzO | H | Me | Moz |
| 11-44 | H | H | H | Cl | Me | Moz |
| 11-45 | H | Me | OH | Me | Me | Moz |
| 11-46 | H | MeO | H | H | Me | Moz |
| 11-47 | H | MeO | H | H | Et | Moz |
| 11-48 | H | MeO | H | H | Pr | Moz |
| 11-49 | H | MeO | H | H | iPr | Moz |
| 11-50 | H | MeO | H | H | iBu | Moz |
| 11-51 | H | EtO | H | H | Me | Moz |
| 11-52 | H | PrO | H | H | Me | Moz |
| 11-53 | H | iPrO | H | H | Me | Moz |
| 11-54 | H | BuO | H | H | Me | Moz |
| 11-55 | H | iBuO | H | H | Me | Moz |
| 11-56 | H | sBuO | H | H | Me | Moz |
| 11-57 | H | tBuO | H | H | Me | Moz |
| 11-58 | H | BuO | H | H | Pr | Moz |
| 11-59 | H | BzO | H | H | Me | Moz |
| 11-60 | H | Me | MeO | H | Me | Moz |
| 11-61 | H | Br | MeO | H | Me | Moz |
| 11-62 | H | F | EtO | H | Me | Moz |
| 11-63 | F | H | F | H | Me | Moz |
| 11-64 | H | F | H | H | Me | Moz |
| 11-65 | H | Me | Cl | H | Me | Moz |
| 11-66 | H | Et | Cl | H | Et | Moz |
| 11-67 | H | H | Et | H | Me | Moz |
| 11-68 | H | Br | H | H | Me | Moz |
| 11-69 | Br | H | $CF_3$ | H | Me | Moz |
| 11-70 | Cl | H | $CF_3$ | H | Me | Moz |
| 11-71 | $CF_3$ | H | H | H | Me | Moz |
| 11-72 | H | $CF_3$ | H | H | Me | Moz |
| 11-73 | Me | Me | Br | H | Me | Moz |
| 11-74 | H | Cl | F | H | Me | Moz |
| 11-75 | H | Br | H | Me | Me | Moz |
| 11-76 | H | tBu | H | H | Me | Moz |
| 11-77 | H | H | OH | H | Me | Moz |
| 11-78 | Me | H | H | H | Me | Moz |
| 11-79 | Cl | Cl | H | H | Me | Moz |
| 11-80 | F | F | F | H | Me | Moz |
| 11-81 | H | BzO | Br | H | Me | Moz |
| 11-82 | Cl | H | H | H | Me | Moz |
| 11-83 | Me | OH | Me | H | Me | Moz |
| 11-84 | Me | OH | Me | Me | Me | Moz |
| 11-85 | Me | OH | Me | Me | Et | Moz |
| 11-86 | Me | AcO | Me | Me | Me | Moz |

TABLE 12

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 12-2 | H | H | H | H | Me | 4BrZ |
| 12-3 | H | H | H | H | Et | 4BrZ |
| 12-4 | H | H | H | H | Pr | 4BrZ |

TABLE 12-continued

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 12-5 | H | H | H | H | iPr | 4BrZ |
| 12-6 | H | H | H | H | Bu | 4BrZ |
| 12-8 | H | H | MeO | H | Me | 4BrZ |
| 12-9 | H | H | MeO | H | Et | 4BrZ |
| 12-10 | H | H | MeO | H | Pr | 4BrZ |
| 12-11 | H | H | MeO | H | iPr | 4BrZ |
| 12-12 | H | H | MeO | H | iBu | 4BrZ |
| 12-13 | H | H | EtO | H | Me | 4BrZ |
| 12-14 | H | H | PrO | H | Me | 4BrZ |
| 12-15 | H | H | iPrO | H | Me | 4BrZ |
| 12-16 | H | H | BuO | H | Me | 4BrZ |
| 12-17 | H | H | iBuO | H | Me | 4BrZ |
| 12-18 | H | H | sBuO | H | Me | 4BrZ |
| 12-19 | H | H | tBuO | H | Me | 4BrZ |
| 12-20 | H | H | BuO | H | Pr | 4BrZ |
| 12-21 | H | H | BzO | H | Me | 4BrZ |
| 12-22 | H | MeO | Me | H | Me | 4BrZ |
| 12-23 | H | MeO | Br | H | Me | 4BrZ |
| 12-24 | H | EtO | F | H | Me | 4BrZ |
| 12-25 | H | F | H | F | Me | 4BrZ |
| 12-26 | H | H | F | H | Me | 4BrZ |
| 12-27 | H | Cl | Me | H | Me | 4BrZ |
| 12-28 | H | Cl | Et | H | Et | 4BrZ |
| 12-29 | H | Et | H | H | Me | 4BrZ |
| 12-30 | H | H | Br | H | Me | 4BrZ |
| 12-31 | H | $CF_3$ | H | Br | Me | 4BrZ |
| 12-32 | H | $CF_3$ | H | Cl | Me | 4BrZ |
| 12-33 | H | H | H | $CF_3$ | Me | 4BrZ |
| 12-34 | H | H | $CF_3$ | H | Me | 4BrZ |
| 12-35 | H | Br | Me | Me | Me | 4BrZ |
| 12-36 | H | F | Cl | H | Me | 4BrZ |
| 12-37 | H | Br | H | Me | Me | 4BrZ |
| 12-38 | H | H | tBu | H | Me | 4BrZ |
| 12-39 | H | OH | H | H | Me | 4BrZ |
| 12-40 | H | H | H | Me | Me | 4BrZ |
| 12-41 | H | H | Cl | Cl | Me | 4BrZ |
| 12-42 | H | F | F | F | Me | 4BrZ |
| 12-43 | H | Br | BzO | H | Me | 4BrZ |
| 12-44 | H | H | H | Cl | Me | 4BrZ |
| 12-45 | H | Me | OH | Me | Me | 4BrZ |
| 12-46 | H | MeO | H | H | Me | 4BrZ |
| 12-47 | H | MeO | H | H | Et | 4BrZ |
| 12-48 | H | MeO | H | H | Pr | 4BrZ |
| 12-49 | H | MeO | H | H | iPr | 4BrZ |
| 12-50 | H | MeO | H | H | iBu | 4BrZ |
| 12-51 | H | EtO | H | H | Me | 4BrZ |
| 12-52 | H | PrO | H | H | Me | 4BrZ |
| 12-53 | H | iPrO | H | H | Me | 4BrZ |
| 12-54 | H | BuO | H | H | Me | 4BrZ |
| 12-55 | H | iBuO | H | H | Me | 4BrZ |
| 12-56 | H | sBuO | H | H | Me | 4BrZ |
| 12-57 | H | tBuO | H | H | Me | 4BrZ |
| 12-58 | H | BuO | H | H | Pr | 4BrZ |
| 12-59 | H | BzO | H | H | Me | 4BrZ |
| 12-60 | H | Me | MeO | H | Me | 4BrZ |
| 12-61 | H | Br | MeO | H | Me | 4BrZ |
| 12-62 | H | F | EtO | H | Me | 4BrZ |
| 12-63 | F | H | F | H | Me | 4BrZ |
| 12-64 | H | F | H | H | Me | 4BrZ |
| 12-65 | H | Me | Cl | H | Me | 4BrZ |
| 12-66 | H | Et | Cl | H | Et | 4BrZ |
| 12-67 | H | H | Et | H | Me | 4BrZ |
| 12-68 | H | Br | H | H | Me | 4BrZ |
| 12-69 | Br | H | $CF_3$ | H | Me | 4BrZ |
| 12-70 | Cl | H | $CF_3$ | H | Me | 4BrZ |
| 12-71 | $CF_3$ | H | H | H | Me | 4BrZ |
| 12-72 | H | $CF_3$ | H | H | Me | 4BrZ |
| 12-73 | Me | Me | Br | H | Me | 4BrZ |
| 12-74 | H | Cl | F | H | Me | 4BrZ |
| 12-75 | H | Br | H | Me | Me | 4BrZ |
| 12-76 | H | tBu | H | H | Me | 4BrZ |
| 12-77 | H | H | OH | H | Me | 4BrZ |
| 12-78 | Me | H | H | H | Me | 4BrZ |
| 12-79 | Cl | Cl | H | H | Me | 4BrZ |
| 12-80 | F | F | H | H | Me | 4BrZ |
| 12-81 | H | BzO | Br | H | Me | 4BrZ |
| 12-82 | Cl | H | H | H | Me | 4BrZ |
| 12-83 | Me | OH | Me | H | Me | 4BrZ |
| 12-84 | Me | OH | Me | Me | Me | 4BrZ |
| 12-85 | Me | OH | Me | Me | Et | 4BrZ |
| 12-86 | Me | AcO | Me | Me | Me | 4BrZ |

TABLE 13

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 13-2 | H | H | H | H | Me | H |
| 13-3 | H | H | H | H | Et | H |
| 13-4 | H | H | H | H | Pr | H |
| 13-5 | H | H | H | H | iPr | H |
| 13-6 | H | H | H | H | Bu | H |
| 13-8 | H | H | MeO | H | Me | H |
| 13-9 | H | H | MeO | H | Et | H |
| 13-10 | H | H | MeO | H | Pr | H |
| 13-11 | H | H | MeO | H | iPr | H |
| 13-12 | H | H | MeO | H | iBu | H |
| 13-13 | H | H | EtO | H | Me | H |
| 13-14 | H | H | PrO | H | Me | H |
| 13-15 | H | H | iPrO | H | Me | H |
| 13-16 | H | H | BuO | H | Me | H |
| 13-17 | H | H | iBuO | H | Me | H |
| 13-18 | H | H | sBuO | H | Me | H |
| 13-19 | H | H | tBuO | H | Me | H |
| 13-20 | H | H | BuO | H | Pr | H |
| 13-21 | H | H | BzO | H | Me | H |
| 13-22 | H | MeO | Me | H | Me | H |
| 13-23 | H | MeO | Br | H | Me | H |
| 13-24 | H | EtO | F | H | Me | H |
| 13-25 | H | F | H | F | Me | H |
| 13-26 | H | H | F | H | Me | H |
| 13-27 | H | Cl | Me | H | Me | H |
| 13-28 | H | Cl | Et | H | Et | H |
| 13-29 | H | Et | H | H | Me | H |
| 13-30 | H | H | Br | H | Me | H |
| 13-31 | H | $CF_3$ | H | Br | Me | H |
| 13-32 | H | $CF_3$ | H | Cl | Me | H |
| 13-33 | H | H | H | $CF_3$ | Me | H |
| 13-34 | H | H | $CF_3$ | H | Me | H |
| 13-35 | H | Br | Me | Me | Me | H |
| 13-36 | H | F | Cl | H | Me | H |
| 13-37 | H | Br | H | Me | Me | H |
| 13-38 | H | H | tBu | H | Me | H |
| 13-39 | H | OH | H | H | Me | H |
| 13-40 | H | H | H | Me | Me | H |
| 13-41 | H | H | Cl | Cl | Me | H |
| 13-42 | H | F | F | F | Me | H |
| 13-43 | H | Br | BzO | H | Me | H |
| 13-44 | H | H | H | Cl | Me | H |
| 13-45 | H | Me | OH | Me | Me | H |
| 13-46 | H | MeO | H | H | Me | H |
| 13-47 | H | MeO | H | H | Et | H |
| 13-48 | H | MeO | H | H | Pr | H |
| 13-49 | H | MeO | H | H | iPr | H |
| 13-50 | H | MeO | H | H | iBu | H |
| 13-51 | H | EtO | H | H | Me | H |
| 13-52 | H | PrO | H | H | Me | H |
| 13-53 | H | iPrO | H | H | Me | H |
| 13-54 | H | BuO | H | H | Me | H |
| 13-55 | H | iBuO | H | H | Me | H |
| 13-56 | H | sBuO | H | H | Me | H |
| 13-57 | H | tBuO | H | H | Me | H |
| 13-58 | H | BuO | H | H | Pr | H |
| 13-59 | H | BzO | H | H | Me | H |
| 13-60 | H | Me | MeO | H | Me | H |
| 13-61 | H | Br | MeO | H | Me | H |
| 13-62 | H | F | EtO | H | Me | H |
| 13-63 | F | H | F | H | Me | H |
| 13-64 | H | F | H | H | Me | H |

TABLE 13-continued

| Exp. Comp.No. | $R^{1c}$ | $R^{2c}$ | $R^{3c}$ | $R^{4c}$ | $R^{7c}$ | $R^{8c}$ |
|---|---|---|---|---|---|---|
| 13-65 | H | Me | Cl | H | Me | H |
| 13-66 | H | Et | Cl | H | Et | H |
| 13-67 | H | H | Et | H | Me | H |
| 13-68 | H | Br | H | H | Me | H |
| 13-69 | Br | H | $CF_3$ | H | Me | H |
| 13-70 | Cl | H | $CF_3$ | H | Me | H |
| 13-71 | $CF_3$ | H | H | H | Me | H |
| 13-72 | H | $CF_3$ | H | H | Me | H |
| 13-73 | Me | Me | Br | H | Me | H |
| 13-74 | H | Cl | F | H | Me | H |
| 13-75 | H | Br | H | Me | Me | H |
| 13-76 | H | tBu | H | H | Me | H |
| 13-77 | H | H | OH | H | Me | H |
| 13-78 | Me | H | H | H | Me | H |
| 13-79 | Cl | Cl | H | H | Me | H |
| 13-80 | F | F | F | H | Me | H |
| 13-81 | H | BzO | Br | H | Me | H |
| 13-82 | Cl | H | H | H | Me | H |
| 13-83 | Me | OH | Me | H | Me | H |
| 13-84 | Me | OH | Me | Me | Me | H |
| 13-85 | Me | OH | Me | Me | Et | H |
| 13-86 | Me | AcO | Me | Me | Me | H |

Preferable exemplification compounds in the tables are those having exemplification compound numbers 9-2, 9-3, 9-4, 9-5, 9-6, 9-8, 9-9, 9-10, 9-11, 9-12, 9-13, 9-14, 9-15, 9-16, 9-17, 9-18, 9-19, 9-20, 9-46, 9-47, 9-48, 9-49, 9-50, 9-51, 9-52, 9-53, 9-54, 9-55, 9-56, 9-57, 9-58, 10-2, 10-3, 10-4, 10-5, 10-6, 10-8, 10-9, 10-10, 10-11, 10-12, 10-13, 10-14, 10-15, 10-16, 10-17, 10-18, 10-19, 10-20, 10-46, 10-47, 10-48, 10-49, 10-50, 10-51, 10-52, 10-53, 10-54, 10-55, 10-56, 10-57, 10-58, 11-2, 11-3, 11-4, 11-5, 11-6, 11-8, 11-9, 11-10, 11-11, 11-12, 11-13, 11-14, 11-15, 11-16, 11-17, 11-18, 11-19, 11-20, 11-46, 11-47, 11-48, 11-49, 11-50, 11-51, 11-52, 11-53, 11-54, 11-55, 11-56, 11-57, 11-58, 12-2, 12-3, 12-4, 12-5, 12-6, 12-8, 12-9, 12-10, 12-11, 12-12, 12-13, 12-14, 12-15, 12-16, 12-17, 12-18, 12-19, 12-20, 12-46, 12-47, 12-48, 12-49, 12-50, 12-51, 12-52, 12-53, 12-54, 12-55, 12-56, 12-57, 12-58, 13-2, 13-3, 13-4, 13-5, 13-6, 13-8, 13-9, 13-10, 13-11, 13-12, 13-13, 13-14, 13-15, 13-16, 13-17, 13-18, 13-19, 13-20, 13-46, 13-47, 13-48, 13-49, 13-50, 13-51, 13-52, 13-53, 13-54, 13-55, 13-56, 13-57 and 13-58,; more preferably 9-8, 9-9, 9-46, 9-47, 13-8, 13-9, 13-46 or 13-47; most preferably 9-8, which is N-[2-[4-(2,4-dioxothiazolidin-5-ylmethyl)phenoxyacetylamino]-5-methoxyphenyl]-N-methylcarbamic acid t-butyl ester.

[4] A process for the preparation of a compound of formula (5) (which is referred to as compound (5) hereinafter) or a pharmaceutically acceptable salt thereof by a reaction of a compound of formula (4) (which is referred to as compound (4) hereinafter) with alkali metal alkoxide,

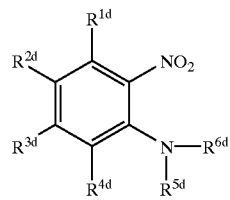

(4)

wherein $R^{1d}$, $R^{2d}$, $R^{3d}$ and $R^{4d}$ are each independently hydrogen, hydroxyl, $C_1$–$C_6$ alkyl, $C_1$–$C_6$ alkoxy, benzyloxy, acetoxy, trifluoromethyl or halogen, and $R^{5d}$ and $R^{6d}$ are each an amino protecting group.

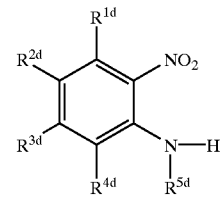

(5)

wherein $R^{1d}$, $R^{2d}$, $R^{3d}$, $R^{4d}$, and $R^{5d}$ are as defined above.

In the process for preparation described above, preferable processes are:

[4-1] a process for the preparation of a compound or a pharmaceutically acceptable salt thereof according to [4] wherein $R^{5d}$ and $R^{6d}$ are each t-butoxycarbonyl, benzyloxycarbonyl, p-methoxybenzyloxycarbonyl or p-bromobenzyloxycarbonyl;

[4-2] a process for the preparation of a compound or a pharmaceutically acceptable salt thereof according to [4] wherein $R^{5d}$ and $R^{6d}$ are each t-butoxycarbonyl;

[4-3] a process for the preparation of a compound or a pharmaceutically acceptable salt thereof according to any one of [4], [4-1] or [4-2] wherein $R^{1d}$, $R^{2d}$, $R^{3d}$ and $R^{4d}$ are each independently hydrogen or $C_1$–$C_4$ alkoxy;

[4-4] a process for the preparation of a compound or a pharmaceutically acceptable salt thereof according to any one of [4], [4-1] or [4-2] wherein $R^{1d}$, $R^{2d}$, $R^{3d}$ and $R^{4d}$ are each independently hydrogen or methoxy; and

[4-5] a process for the preparation of a compound or a pharmaceutically acceptable salt thereof according to [4] wherein $R^{1d}$, $R^{2d}$ and $R^{4d}$ are each hydrogen, $R^{3d}$ is methoxy, and $R^{5d}$ and $R^{6d}$ are each t-butoxycarbonyl.

The $C_1$–$C_6$ alkyl group of compounds (4) and (5) is as defined in [1], preferably the alkyl group is $C_1$–$C_4$ alkyl, more preferably the alkyl group is methyl or ethyl and most preferably the alkyl group is methyl.

The $C_1$–$C_6$ alkoxy group of compounds (4) and (5) is as defined in [1], preferably the alkoxy group is $C_1$–$C_4$ alkoxy, more preferably the alkoxy group is methoxy or ethoxy and most preferably the alkoxy group is methoxy.

The halogen atom of compounds (4) and (5) is defined as in [1], preferably the halogen atom is fluorine, chlorine or bromine.

The amino protecting group of compounds (4) and (5) is as defined in [1], preferably the protecting group is t-butoxycarbonyl, benzyl, p-methoxybenzyl, p-bromobenzyl, benzyloxycarbonyl, p-methoxybenzyloxycarbonyl or p-bromobenzyloxycarbonyl, more preferably one is t-butoxycarbonyl, benzyloxycarbonyl, p-methoxybenzyloxycarbonyl or p-bromobenzyloxycarbonyl, most preferably one is t-butoxycarbonyl.

In compounds (4) and (5), preferably $R^{1d}$, $R^{2d}$, $R^{3d}$ and $R^{4d}$ are each independently hydrogen or $C_1$–$C_4$ alkoxy; more preferably $R^{1d}$, $R^{2d}$, $R^{3d}$ and $R^{4d}$ are each independently hydrogen or methoxy; most preferably $R^{1d}$, $R^{2d}$ and $R^{4d}$ are each hydrogen and most preferably $R^{3d}$ is methoxy.

In compound (4), preferably $R^{5d}$ and $R^{6d}$ are each independently t-butoxycarbonyl, benzyloxycarbonyl, p-methoxybenzyloxycarbonyl or p-bromobenzyloxycarbonyl; more preferably $R^{5d}$ and $R^{6d}$ are each t-butoxycarbonyl.

In compound (5), preferably $R^{5d}$ is t-butoxycarbonyl, benzyloxycarbonyl, p-methoxybenzyloxycarbonyl or p-bromobenzyloxycarbonyl; more preferably $R^{5d}$ is t-butoxycarbonyl.

Pharmaceutically acceptable salts of compound (5) are as defined in [1].

[5] A process for the preparation of a benzimidazole derivative of formula (9) (which is referred to as compound (9) hereinafter) or a pharmaceutically acceptable salt thereof by condensation of a compound of formula (6) (which is referred to as compound (6) hereinafter) with a compound of formula (7) (which is referred to as compound (7) hereinafter) in the presence of a condensing agent to afford a compound of formula (8) (which is referred to as compound (8) hereinafter), followed by, if necessary removal of the amino protecting group of compound (8), and then cyclization of compound (8) in the presence of an acid,

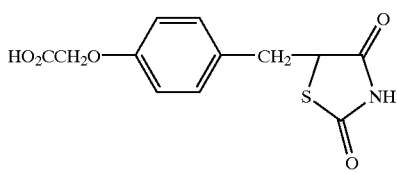

(6)

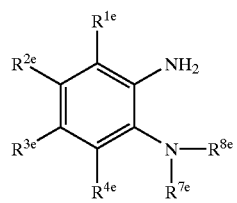

(7)

wherein $R^{1e}$, $R^{2e}$, $R^{3e}$ and $R^{4e}$ are each independently hydrogen, hydroxyl, $C_1$–$C_6$ alkyl, $C_1$–$C_6$ alkoxy, benzyloxy, acetoxy, trifluoromethyl or halogen, $R^{7e}$ is $C_1$–$C_6$ alkyl and $R^{8e}$ is hydrogen or an amino protecting group,

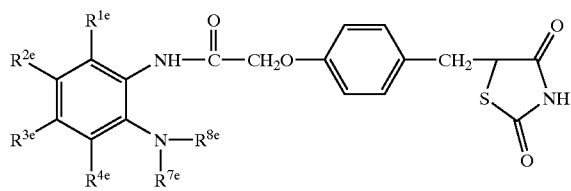

(8)

wherein $R^{1e}$, $R^{2e}$, $R^{3e}$, $R^{4e}$, $R^{7e}$ and $R^{8e}$ are as defined above

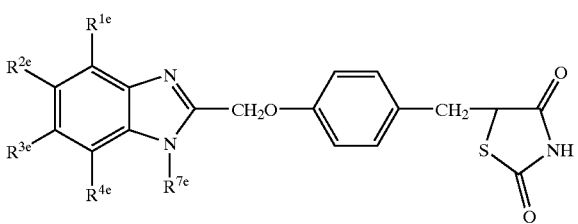

(9)

wherein $R^{1e}$, $R^{2e}$, $R^{3e}$, $R^{4e}$, and $R^{7e}$ are as defined above.

In the process for preparation described above, preferable processes are:

[5-1] a process for the preparation of a benzimidazole derivative or a pharmaceutically acceptable salt thereof according to [5] wherein $R^{8e}$ is hydrogen, t-butoxycarbonyl, benzyloxycarbonyl, p-methoxybenzyloxycarbonyl or p-bromobenzyloxycarbonyl;

[5-2] a process for the preparation of a benzimidazole derivative or a pharmaceutically acceptable salt thereof according to [5] wherein $R^{8e}$ is hydrogen or t-butoxycarbonyl;

[5-3] a process for the preparation of a benzimidazole derivative or a pharmaceutically acceptable salt thereof according to [5] wherein $R^{8e}$ is t-butoxycarbonyl;

[5-4] a process for the preparation of a benzimidazole derivative or a pharmaceutically acceptable salt thereof according to any one of [5], [5-1], [5-2] or [5-3] wherein $R^{7e}$ is $C_1$–$C_4$ alkyl;

[5-5] a process for the preparation of a benzimidazole derivative or a pharmaceutically acceptable salt thereof according to any one of [5], [5-1], [5-2] or [5-3] wherein $R^{7e}$ is $C_1$–$C_2$ alkyl;

[5-6] a process for the preparation of a benzimidazole derivative or a pharmaceutically acceptable salt thereof according to any one of [5], [5-1], [5-2] or [5-3] wherein $R^{7e}$ is methyl;

[5-7] a process for the preparation of a benzimidazole derivative or a pharmaceutically acceptable salt thereof according to any one of [5], [5-1], [5-2], [5-3], [5-4], [5-5] or [5-6] wherein $R^{1e}$, $R^{2e}$, $R^{3e}$ and $R^{4e}$ are each independently hydrogen or $C_1$–$C_4$ alkoxy;

[5-8] a process for the preparation of a benzimidazole derivative or a pharmaceutically acceptable salt thereof according to any one of [5], [5-1], [5-2], [5-3], [5-4], [5-5] or [5-6] wherein $R^{1e}$, $R^{2e}$, $R^{3e}$ and $R^{4e}$ are each independently hydrogen or methoxy; and

[5-9] a process for the preparation of a benzimidazole derivative or a pharmaceutically acceptable salt thereof according to [5] wherein $R^{1e}$, $R^{2e}$ and $R^{4e}$ are each hydrogen, $R^{3e}$ is methoxy and $R^{7e}$ is methyl.

The $C_1$–$C_6$ alkyl group of compounds (7), (8) and (9) is as defined in [1], preferably the alkyl group is $C_1$–$C_4$ alkyl, more preferably the alkyl group is methyl or ethyl and most preferably the alkyl group is methyl.

The $C_1$–$C_6$ alkoxy group of compounds (7), (8) and (9) is as defined in [1], preferably the alkoxy group is $C_1$–$C_4$ alkoxy, more preferably the alkoxy group is methoxy or ethoxy and most preferably the alkoxy group is methoxy.

The halogen atom of compounds (7), (8) and (9) is defined as in [1], preferably the halogen atom is fluorine, chlorine or bromine.

The amino protecting group of compounds (7) and (8) is as defined in [1], preferably the protecting group is t-butoxycarbonyl, benzyl, p-methoxybenzyl, p-bromobenzyl, benzyloxycarbonyl, p-methoxybenzyloxycarbonyl or p-bromobenzyloxycarbonyl, more preferably one is t-butoxycarbonyl, benzyloxycarbonyl, p-methoxybenzyloxycarbonyl or p-bromobenzyloxycarbonyl, most preferably one is t-butoxycarbonyl.

In compounds (7), (8) and (9), preferably $R^{1e}$, $R^{2e}$, $R^{3e}$ and $R^{4e}$ are each independently hydrogen or $C_1$–$C_4$ alkoxy; more preferably $R^{1e}$, $R^{2e}$, $R^{3e}$ and $R^{4e}$ are each independently hydrogen or methoxy; most preferably $R^{1e}$, $R^{2e}$ and $R^{4e}$ are each hydrogen and most preferably $R^{3e}$ is methoxy; and preferably $R^{7e}$ is $C_1$–$C_4$ alkyl, more preferably $R^{7e}$ is $C_1$–$C_2$ alkyl, most preferably $R^{7e}$ is methyl.

In compounds (7) and (8), preferably $R^{8e}$ is hydrogen, t-butoxycarbonyl, benzyloxycarbonyl, p-methoxybenzyloxycarbonyl or p-bromobenzyloxycarbonyl; more preferably $R^{8e}$ is hydrogen or t-butoxycarbonyl and most preferably $R^{8e}$ is t-butoxycarbonyl.

The pharmaceutically acceptable salts of compound (9) are as defined in [1].

The processes for the preparation of intermediates [1], [2] and [3] of this invention and the processes [4] and [5] of this invention are described in detail below.

[1] The compound (1) can be prepared according to the following scheme,

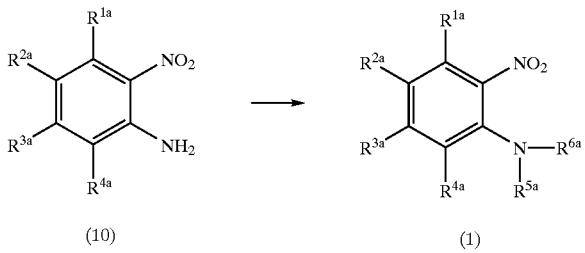

wherein $R^{1a}$, $R^{2a}$, $R^{3a}$, $R^{4a}$, $R^{5a}$ and $R^{6a}$ are as defined above.

In this step a compound of formula (1) is obtained by the reaction of a compound of formula (10) with a reagent for introducing an amino protecting group in the presence of a base in an inert solvent.

Suitable examples of the reagent for introducing an amino protecting group include halide derivatives or acid anhydrides having amino protecting moieties, for example t-butoxycarbonylhalides such as t-butoxycarbonylchloride and t-butoxycarbonylbromide; di-t-butoxycarbonyldicarbonate; trityl halides such as trityl chloride and trityl bromide; $C_6$–$C_{10}$ arylmethyl halides, which are optionally substituted with $C_1$–$C_6$ alkyl, $C_1$–$C_6$ alkoxy or halogen, such as benzyl chloride, benzyl bromide, methylbenzyl chloride, methoxybenzyl chloride, methoxybenzyl bromide, bromobenzyl chloride and naphthylmethyl chloride; and $C_6$–$C_{10}$ arylmethyloxycarbonylhalides, which are optionally substituted with $C_1$–$C_6$ alkyl, $C_1$–$C_6$ alkoxy or halogen, such as benzyloxycarbonylchloride, benzyloxycarbonylbromide, methylbenzyloxyczarbonylchloride, methoxybenzyloxycarbonylbromide, bromobenzyloxycarbonylchloride and naphthylmethyloxycarbonylchloride. Of these reagents, t-butoxycarbonylhalides, di-t-butoxycarbonyldicarbonate and benzyloxycarbonylhalides which are optionally substituted with methoxy or bromine are preferred. t-Butoxycarbonylchloride, t-butoxycarbonylbromide and di-t-butoxycarbonyldicarbonate are more preferred, and di-t-butoxycarbonyldicarbonate are most preferred.

The examples of the base used in this step include alkali metal hydroxides such as lithium hydroxide, sodium hydroxide and potassium hydroxide; alkaline earth metal hydroxides such as calcium hydroxide, barium hydroxide and magnesium hydroxide; alkali metal alkoxides such as lithium ethoxide, sodium methoxide, sodium ethoxide and potassium t-butoxide; alkai metal or alkaline earth metal hydrides such as lithium hydride, sodium hydride, potassium hydride and calcium hydride; aliphatic amines such as triethylamine, diisopropylethylamine and 1,8-diazabicyclo[5.4.0]undec-7-ene (DBU); aromatic amines such as pyridine, 4-(N,N-dimethylamino)pyridine, aniline and N,N-dimethylaniline. Aliphatic amines, aromatic amines, alkali metal alkoxides and alkali metal or alkali earth metal hydrides are preferred. Triethylamine, pyridine, 4-(N,N-dimethylamino)pyridine, potassium t-butoxide and sodium hydride are more preferred, and 4-(N,N-dimethylamino)pyridine is most preferred.

The amount of a base used is between 0.01 and 2 equivalents, preferably between 0.02 and 0.1 equivalents.

The solvent employed in this step is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; esters such as methyl acetate, ethyl acetate, methyl propionate and ethyl propionate; nitriles such as acetonitrile; amides such as N,N-dimethylformamide and N,N-dimethylacetamide; sulfoxides such as dimethyl sulfoxide and mixtures thereof. Aromatic hydrocarbons, halogenated hydrocarbons, ethers, esters, amides and nitriles are preferred. Halogenated hydrocarbons, ethers, esters, amides and nitriles are more preferred, and methylene chloride and ethyl acetate are most preferred.

The reaction temperature employed in this step depends upon various factors such as the nature of the starting materials and the solvent. However, it is usually between −10° C. and 100° C., and is preferably between 0° C. and 50° C.

The reaction time employed in this step depends on the reaction temperature and the like. It is typically from 10 minutes to 10 hours, and preferably from 30 minutes to 5 hours.

The desired compound in this step can be isolated from the reaction mixture by a conventional technique, for example, when there is insoluble material in the reaction mixture, the reaction mixture is filtered, the filtrate, if necessary, is neutralized and cooled to afford the desired crystals which are collected by filtration or the solvent of the filtrate is evaporated off and the residue is partitioned between water and an organic solvent immiscible with water, the organic layer is dried over anhydrous magnesium sulfate and concentrated to give the desired product. The desired product thus isolated can be, if necessary, further purified through a conventional technique such as recrystallization or chromatography.

[2] The compound (2) can be prepared according to the following scheme,

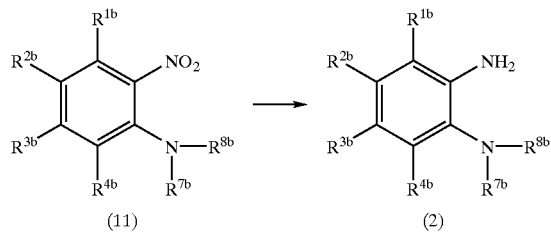

wherein $R^{1b}$, $R^{2b}$, $R^{3b}$, $R^{4b}$, $R^{7b}$ and $R^{8b}$ are as defined above.

In this step a compound of formula (2) is obtained by the reaction of a compound of formula (11) (hereinafter referred to as compound (11)) with a reducing reagent, capable of reducing a nitro group to an amino group, in an inert solvent.

The reducing agent employed in this step is not particularly limited provided that it can reduce a nitro group into an amino group. A suitable example of the reducing reagent is a combination of hydrogen and a catalyst which is usually used in catalytic reduction. Examples of the catalyst for catalytic reduction include palladium on carbon, palladium black, Raney nickel, platinum oxide, platinum black, rhodium-aluminum oxide, triphenylphosphine-rhodium chloride, and palladium-barium sulfate. Palladium on carbon is preferred.

The pressure of hydrogen employed in this step is not particularly limited, however it is usually between 1 to 10 atmospheres, preferably between 1 and 3 atmospheres.

The solvent employed in this step is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; alcohols such as methanol, ethanol, propanol, isopropanol and butanol; esters such as methyl acetate, ethyl acetate, methyl propionate and ethyl propionate; amides such as N,N-dimethylformamide and N,N-dimethylacetamide; sulfoxides such as dimethyl sulfoxide and mixtures thereof. Aromatic hydrocarbons, halogenated hydrocarbons, ethers, alcohols, alcohols containing water and amides are preferred. Toluene and methanol are particularly preferred.

The reaction temperature employed in this step depends upon various factors such as the nature of the starting materials, the catalyst and the solvent. However, it is usually between 0° C. and 100° C., and is preferably between 10° C. and 60° C.

The reaction time employed in this step depends on the reaction temperature and the like. It is typically from 5 minutes to 24 hours, and preferably from 10 minutes to 10 hours.

The desired compound in this step can be isolated from the reaction mixture by a conventional technique, for example, when there is insoluble material in the reaction mixture, the reaction mixture is filtered, the filtrate, if necessary, is neutralized and cooled to afford the desired crystals which are collected by filtration or the solvent of the filtrate is evaporated off and the residue is partitioned between water and an organic solvent immiscible with water, the organic layer is dried over anhydrous magnesium sulfate and concentrated to give the desired product. The desired product thus isolated can be, if necessary, further purified through a conventional technique such as recrystallization or chromatography.

[3] Compound (3) can be prepared according to step 1 and step 2 described in process [5].

[4] The compound (5) can be prepared using compound (4) as a starting material according to the following scheme,

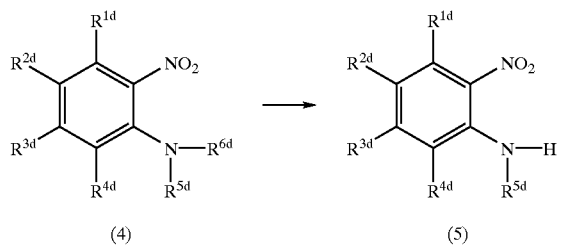

wherein $R^{1d}$, $R^{2d}$, $R^{3d}$, $R^{4d}$, $R^{5d}$ and $R^{6d}$ are as defined above.

In this step a compound of formula (5) is obtained by the reaction of a compound of formula (4) with an alkali metal alkoxide in an inert solvent.

The solvent employed in this step is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; alcohols such as methanol, ethanol, propanol, isopropanol and butanol; esters such as methyl acetate, ethyl acetate, methyl propionate and ethyl propionate; nitrites such as acetonitrile; amides such as N,N-dimethylformamide and N,N-dimethylacetamide; sulfoxides such as dimethyl sulfoxide and mixtures thereof. Aromatic hydrocarbons, ethers, alcohols, amides, nitriles and mixtures thereof are preferred. Aromatic hydrocarbons, alcohols and mixtures thereof are more preferred. A mixture of toluene and methanol is particularly preferred.

Examples of the alkali metal alkoxide employed in this step include lithium ethoxide, sodium methoxide, sodium ethoxide, sodium t-butoxide and potassium t-butoxide. Sodium methoxide is preferred.

The amount of the alkali metal alkoxide is between 0.1 and 10 equivalents, and preferably between 0.5 and 1 equivalent.

The reaction temperature employed in this step is between −10° C. and 100° C., and is preferably between 0° C. and 50° C.

The reaction time employed in this step depends on the reaction temperature and the like. It is usually from 10 minutes to 10 hours, and preferably from 30 minutes to 5 hours.

The desired compound (5) in this step can be isolated from the reaction mixture by a conventional technique, for example, when there is insoluble material in the reaction mixture, the reaction mixture is filtered, the filtrate, if necessary, is neutralized and cooled to afford the desired crystals which are collected by filtration or the solvent of the filtrate is evaporated off and the residue is partitioned between water and an organic solvent immiscible with water, the organic layer is dried over anhydrous magnesium sulfate and concentrated to give the desired product. The desired product thus isolated can be, if necessary, further purified through a conventional technique such as recrystallization or chromatography.

Of the processes for the preparation of compound (5) described above, preferable processes comprise the reaction of compound (4) with lithium ethoxide, sodium methoxide, sodium ethoxide, or potassium t-butoxide in a solvent such as an aromatic hydrocarbon, an alcohol or mixtures thereof, to give compound (5).

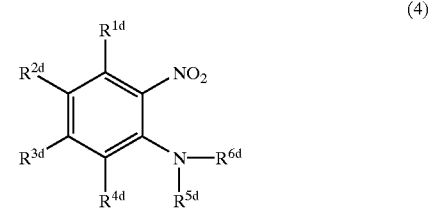

(5)

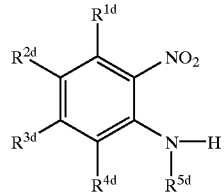

More preferable processes comprise the reaction of compound (4) with sodium methoxide in a mixture of toluene and methanol to give compound (5).

(4)

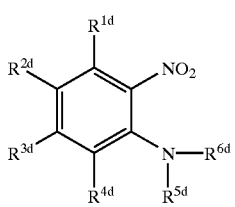

(5)

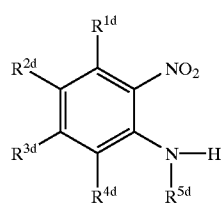

[5] The compound (9) can be prepared by using compound (6) and compound (7) as starting materials according to the three step reactions shown in the following scheme,

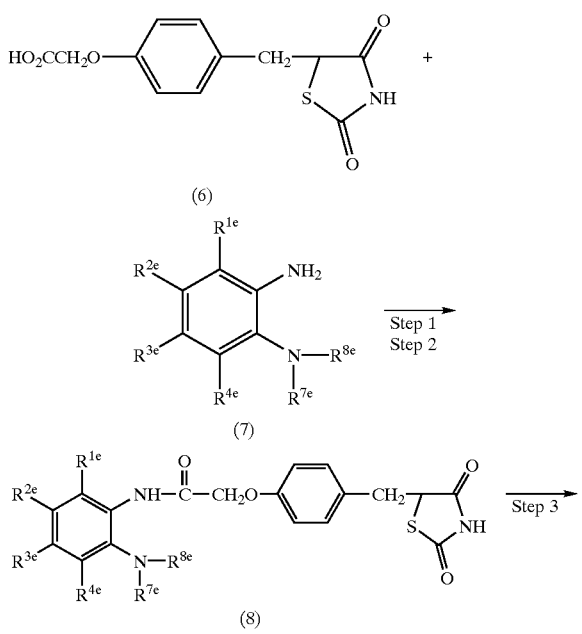

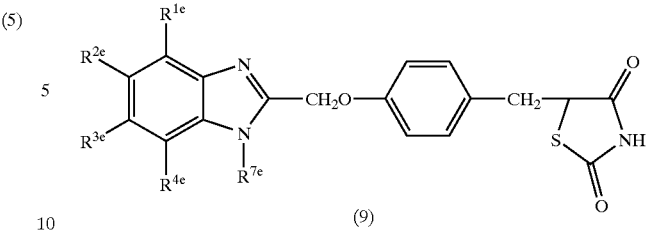

(9)

wherein $R^{1e}$, $R^{2e}$, $R^{3e}$, $R^{4e}$, $R^{7e}$ and $R^{8e}$ are as defined above.

In this scheme compound (9) is obtained by the condensation of a compound (6) with a compound (7) in the presence of a coupling reagent to afford compound (8) (step 1), if necessary, removal of a protecting group of amino (step 2), followed by cyclization of compound (8) in the presence of an acid (step 3). Procedures of each step are described in detail hereinafter.

(Step 1)

In this step compound (8) is obtained by condensation of compound (6) with compound (7) in the presence of a coupling reagent and a base in an inert solvent.

The coupling reagent employed in step I is not particularly limited provided that it can condense a carboxylic acid with an amine to afford an amide. Examples of the coupling reagent include cyclic anhydrides of $C_1$–$C_4$ alkylphosphonic acid such as cyclic anhydrides of methylphophonic acid, ethylphosphonic acid, propylphosphonic acid and butylphosphonic acid; $C_1$–$C_4$ alkylphosphoryl cyanides such as dimethylphosphoryl cyanide, diethylphosphoryl cyanide and dibutylphosphoryl cyanide; and $C_6$–$C_{10}$ arylphosphoryl azides such as diphenylphosphoryl azide, ditolylphosphoryl azide and dinaphthylphosphoryl azide. Cyclic anhydrides of $C_2$–$C_3$ alkylphosphonic acids, diethylphosphonic cyanide and diphenylphosphoryl azide are preferred. Cyclic anhydride of propylphosphonic acid is particularly preferred.

The examples of the base used in step 1 include alkali metal hydroxides such as lithium hydroxide, sodium hydroxide and potassium hydroxide; alkaline earth metal hydroxides such as calcium hydroxide, barium hydroxide and magnesium hydroxide; alkali metal alkoxide such as lithium ethoxide, sodium methoxide, sodium ethoxide and potassium t-butoxide; alkali metal or alkaline earth metal hydrides such as lithium hydride, sodium hydride, potassium hydride and calcium hydride; aliphatic amines such as triethylamine, diisopropylethylamine and 1,8-diazabicyclo [5.4.0]undec-7-ene (DBU); aromatic amines such as pyridine, 4-(N,N-dimethylamino)pyridine, aniline and N,N-dimethylaniline. Aliphatic amines and aromatic amnines are preferred. Triethylamine and diisopropylamine are more preferred.

The amount of base used is between 1 and 3 equivalents, preferably between 1.2 and 2 equivalents.

The solvent employed in step 1 is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; esters such as methyl acetate, ethyl acetate, methyl propionate and ethyl propionate; nitriles such as acetonitrile; amides such as N,N- dimethylformamide and N,N-dimethylacetamide; sulfoxides such as dimethyl sulfoxide and mixtures thereof. Halogenated hydrocarbons, ethers, amides and nitriles are preferred. Halogenated hydrocarbons and nitrites are more preferred, and methylene chloride and acetonitrile are most preferred.

The reaction temperature employed in step 1 is usually between −20° C. and 100° C., and is preferably between −10° C. and 30° C.

The reaction time employed in step 1 depends on the reaction temperature and the like. It is typically from 15 minutes to 10 hours, and preferably from 30 minutes to 5 hours.

The desired compound in step 1 can be isolated from the reaction mixture by a conventional technique, for example, the reaction mixture is appropriately neutralized and concentrated and the residue is partitioned between water and an organic solvent immiscible with water, the organic layer is dried over anhydrous magnesium sulfate and concentrated to give the desired product. The desired product thus isolated can be, if necessary, further purified through a conventional technique such as recrystallization or chromatography.

(Step 2)

In step 2 an amino protecting group of amino in compound (8), if necessary, is removed according to conventional techniques known to those skilled in the art, for example, by using an acid, a base or a reducing agent depending on the type of amino protecting group.

When the amino protecting group is a t-butoxycarbonyl or trityl group, said protecting group can be removed by treating with an acid in an inert solvent.

Examples of the acid employed in the removal of the amino protecting group include inorganic acids such as hydrogen chloride, nitric acid, hydrochloric acid, sulfuric acid and phosphoric acid; organic acids such as acetic acid, trifluoroacetic acid methanesulfonic acid and p-toluenesulfonic acid; Lewis acids such as boron trifluoride; acidic cationic ion-exchange resins such as Dowex 50W (trade mark). Of these acids, inorganic acids and organic acids are preferred. Hydrochloric acid, sulfuric acid, phosphoric acid and trifluoroacetic acid are more preferred, and hydrochloric acid is most preferred.

The solvent employed in step 2 is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; alcohols such as methanol, ethanol, propanol, isopropanol and butanol; esters such as methyl acetate, ethyl acetate, methyl propionate and ethyl propionate; nitriles such as acetonitrile; amides such as N,N-dimethylformamide and N,N-dimethylacetamide; sulfoxides such as dimethyl sulfoxide and mixtures thereof. Aromatic hydrocarbons, alcohols and esters are preferred. Alcohols and esters are more preferred, and methanol, ethanol and ethyl acetate are particularly preferred.

The reaction temperature employed in step 2 depends upon various factors such as the nature of the starting materials, solvents and acids. However it is usually between 0° C. and 150° C., and is preferably between 10° C. and 100° C.

The reaction time employed in step 2 depends on the reaction temperature and the like. It is typically from 5 minutes to 24 hours, and preferably from 10 minutes to 10 hours.

When the amino protecting group of compound (8) is $C_6$–$C_{10}$ aryl-methyl or $C_6$–$C_{10}$ aryl-methyloxycarbonyl, both of which may be optionally substituted, said protecting group can be removed by treating with a reducing reagent in an inert solvent (preferably treating with hydrogen in the presence of a catalytic reduction catalyst).

The catalytic reduction catalyst employed in step 2 is not particularly limited provided that it can usually use in catalytic reduction. Examples of the catalyst include palladium on carbon, palladium black, Raney nickel, platinum oxide, platinum black, rhodium-aluminum oxide, triphenylphosphine-rhodium chloride, and palladium-barium sulfate, of which palladium on carbon is preferred.

The solvent employed in step 2 is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; halogenated hydrocarbons such as methylene chloride, chloroform, carbon tetrachloride and dichloroethane; ethers such as diethyl ether, tetrahydrofuran, 1,4-dioxane and 1,2-dimethoxyethane; alcohols such as methanol, ethanol, propanol, isopropanol and butanol; esters such as methyl acetate, ethyl acetate, methyl propionate and ethyl propionate; amides such as N,N-dimethylformamide and N,N-dimethylacetanide; sulfoxides such as dimethyl sulfoxide and mixtures thereof. Aromatic hydrocarbons, ethers, alcohols, alcohols containing water and amides are preferred. Toluene and methanol are particularly preferred.

The pressure of hydrogen employed in step 2 is not particularly limited, however it is usually between 1 and 10 atmospheres, preferably between 1 and 3 atmospheres.

The reaction temperature employed in step 2 depends upon various factors such as the nature of the starting materials, the catalyst and the solvent. However, it is usually between 0° C. and 100° C., and is preferably between 10° C. and 60° C.

The reaction time employed in step 2 depends on the reaction temperature and the like. It is typically from 5 minutes to 24 hours, and preferably from 10 minutes to 10 hours.

The desired compound in this step can be isolated from the reaction mixture by a conventional technique, for example, when there is insoluble material in the reaction mixture, the reaction mixture is filtered, the filtrate, if necessary, is neutralized and cooled to afford the desired crystals which are collected by filtration or the solvent of the filtrate is evaporated off and the residue is partitioned between water and an organic solvent immiscible with water, the organic layer is dried over anhydrous magnesium sulfate and concentrated to give the desired product. The desired product thus isolated can be, if necessary, further purified through a conventional technique such as recrystallization or chromatography.

(Step 3)

In this step compound (9) is obtained by cyclization of a compound (8) (if necessary, a compound from which has been removed an amino protecting group) in the presence of an acid in an inert solvent.

This step can be accomplished by a similar procedure to that described in step 2 which is removal of an amino protecting group such as t-butoxycarbonyl or trityl.

When compound (8), which has an amino protecting group such as t-butoxycarbonyl or trityl, is treated with an acid in step 2, removal of said amino protecting group and cyclization take place at the same time to afford an acid addition salt of compound (9).

Of the processes for the preparation of compound (9) described above, preferable processes comprise the condensation of a compound (6) with a compound (7) in the presence of a coupling reagent such as a cyclic anhydride of $C_2$–$C_3$ alkylphosphonic acid, diethylphosphoryl cyanide or diphenylphosphoryl azide and a base such as an aliphatic amine or aromatic amine in a solvent such as a halogenated hydrocarbon or a nitrile to afford compound (8), followed by removal of the amino protecting group and cyclization of compound (8) in the presence of an acid such as hydrochloric acid, sulfuric acid, phosphoric acid or trifluoroacetic acid to give a benzimidazole compound (9) or a pharmaceutically acceptable salt thereof or followed by removal of the amino protecting group of compound (8) through catalytic hydrogenation in the presence of a catalyst such as palladium on carbon, palladium black, Raney nickel, platinum oxide, triphenylphosphine-rhodium chloride or palladium-barium sulfate in a solvent such as an aromatic hydrocarbon, an ether, an alcohol or an alcohol containing water and by cyclization of the deprotected compound (8) in the presence of an acid such as hydrochloric acid, sulfuric acid, phosphoric acid or trifluoroacetic acid in a solvent such as an alcohol or an ester to give a benzimidazole compound (9) or a pharmaceutically acceptable salt thereof.

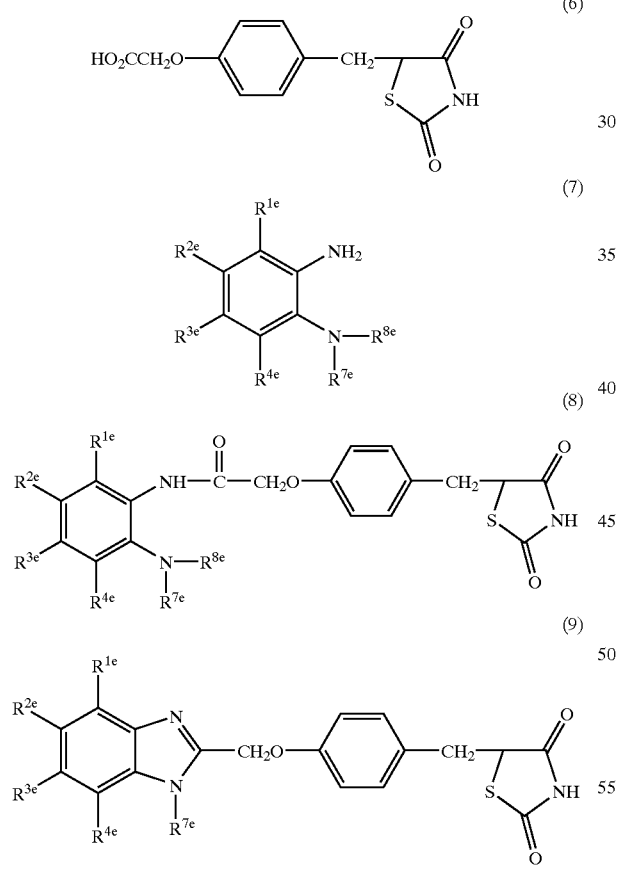

More preferable processes comprise the condensation of a compound (6) with a compound (7) in the presence of the cyclic anhydride of propylphosphonic acid and a base such as triethylamine or diisopropylethylamine in a solvent such as methylene chloride or acetonitrile to afford a compound (8), followed by removal of the amino protecting group and cyclization of compound (8) in the presence of hydrochloric acid to give a benzimidazole compound (9) or a pharmaceutically acceptable salt thereof or followed by removal of the amino protecting group of compound (8) through catalytic hydrogenation in the presence of palladium on carbon in a solvent such as toluene or methanol and by cyclization of the deprotected compound (8) in the presence of hydrochloric acid in a solvent such as methanol, ethanol or ethyl acetate to give a benzimidazole compound (9) or a pharmaceutically acceptable salt thereof.

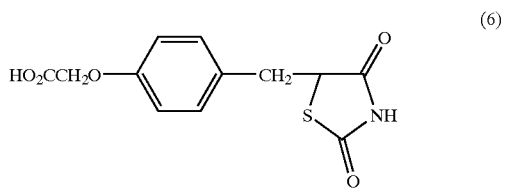

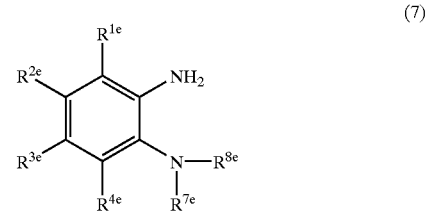

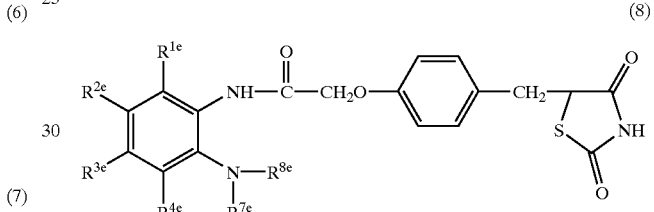

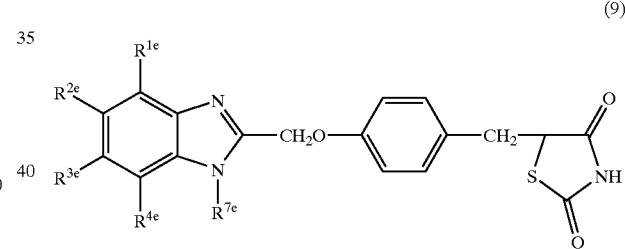

Starting materials of [1] to [5] described above are prepared as follows.

Starting materials of formula (10) described in [1] are known compounds or can be prepared by methods known to those skilled in the art (for example Japanese Patent Application Publication Hei 9-295970 or U.S. Pat. No. 5,886, 014).

Starting materials of formula (11) described in [2] can be prepared by method A described below using compounds obtained in [4] as starting materials.

Starting materials of formula (4) described in [4] can be prepared by the methods described in [1].

Starting materials of formula (6) described in [5] can be prepared by method B described below. Starting materials of formula (7), wherein $R^{8e}$ is an amino protecting group, can be prepared by the methods described [2] and starting materials of formula (7), wherein $R^{8e}$ is hydrogen, can be prepared by method C described below.

(Method A)

Compounds of formula (11) are prepared by method A, wherein

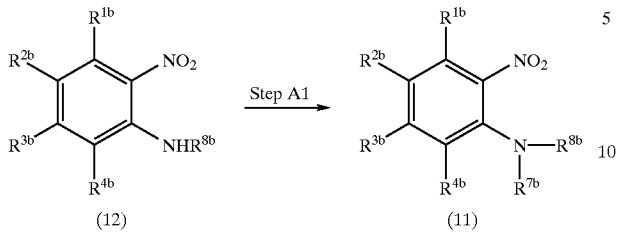

$R^{1b}$, $R^{2b}$, $R^{3b}$, $R^{4b}$, $R^{7b}$ and $R^{8b}$ are as defined above.

Method A comprises the reaction of a compound of formula (12) with an alkylating reagent in the presence of a base in an inert solvent.

Examples of the alkylating reagent employed in method A include $C_1$–$C_6$ alkyl halides such as methyl iodide, ethyl iodide, propyl iodide, butyl bromide, butyl iodide, pentyl chloride, pentyl iodide, hexyl bromide and hexyl bromide or di-$C_1$–$C_6$ alkyl sulfates such as dimethyl sulfate, diethyl sulfate, dipropyl sulfate, dibutyl sulfate and dihexyl sulfate. Of these alkylating reagents $C_1$–$C_2$ alkyl halides and di-$C_1$–$C_2$ alkyl sulfates are preferred and dimethyl sulfate is particularly preferred.

The amount of the alkylating reagent used in Method A is between 1 and 3 equivalents, preferably between 1.2 and 2 equivalents.

The examples of the base used in method A include alkali metal hydroxides such as lithium hydroxide, sodium hydroxide and potassium hydroxide; alkaline earth metal hydroxides such as calcium hydroxide, barium hydroxide and magnesium hydroxide; alkali metal alkoxides such as lithium ethoxide, sodium methoxide, sodium ethoxide and potassium t-butoxide; alkai metal or alkaline earth metal hydrides such as lithium hydride, sodium hydride, potassium hydride and calcium hydride; aliphatic amines such as triethylamine, diisopropylethylamine and 1,8-diazabicyclo[5.4.0]undec-7-ene (DBU); and aromatic amines such as pyridine, 4-(N,N-dimethylamino)pyridine, aniline and N,N-dimethylaniline. Of these bases, alkali metal alkoxides and alkali metal hydrides are preferred, and potassium t-butoxide and sodium hydride are particularly preferred.

The amount of base used in method A is between 1 and 10 equivalents, preferably between 1.2 and 2 equivalents.

The solvent employed in Method A is not particularly limited provided that it has no adverse effect on the reaction and dissolves the starting materials to at least some extent. Suitable solvents are aliphatic hydrocarbons such as hexane, heptane and petroleum ether; aromatic hydrocarbons such as benzene, toluene, xylene and mesitylene; ethers such as diethyl ether, tetrahydrofuran, 1,4dioxane and 1,2-dimethoxyethane; amides such as N,N-dimethylformamide and N,N-dimethylacetamide; and mixtures thereof. Of these solvents, ethers and amides are preferred and tetrahydrofuran and N,N-dimethylformamide are particularly preferred.

The reaction temperature employed in method A depends upon various factors such as the nature of the starting materials and the solvent. However, it is usually between –20° C. and 100° C., and is preferably between –10° C. and 40° C.

The reaction time employed in method A depends on the reaction temperature and the like. However, it is usually from 10 minutes to 10 hours and preferably from 15 minutes to 3 hours.

(Method B)

Compounds of formula (6) are prepared by method B, wherein

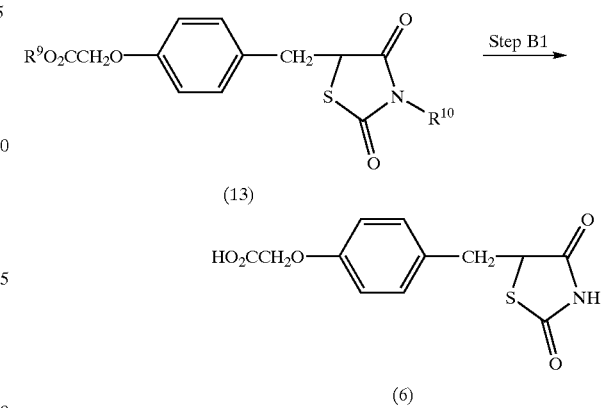

$R^9$ is $C_1$–$C_6$ alkyl and $R^{10}$ is hydrogen or an amino protecting group.

Method B comprises, if necessary, the removal of an amino protecting group from compound (13), followed by hydrolysis of the product or compound (13).

The removal reaction of the amino protecting group can be accomplished using similar procedures to those described in step 2.

The hydrolysis can be accomplished using a conventional technique known to those skilled in organic syntheses by using an acid or a base in an inert solvent containing water.

Examples of the acid employed in method B include the same acids as described in step 2, the process of which is the reaction to remove an amino protecting group. Examples of a base employed in method B include alkali metal hydroxides such as lithium hydroxide, sodium hydroxide and potassium hydroxide and alkali metal carbonates such as sodium carbonate and potassium carbonate. Of these bases, sodium hydroxide and potassium hydroxide are preferred.

The inert solvent containing water employed in Method B is not particularly limited provided that it has no adverse effect on the reaction. Suitable inert solvents are aliphatic hydrocarbons such as hexane and cyclohexane; aromatic hydrocarbons such as benzene, toluene and xylene; ethers such as diethyl ether, tetrahydrofuran and 1,4dioxane; alcohols such as methanol, ethanol, propanol and isopropanol; and carboxylic acids such as acetic acid. Of these solvents, when an acid is used in method B, alcohols and carboxylic acids are preferred and methanol and acetic acid are particularly preferred and when a base is used in method B alcohols are preferred and methanol is particularly preferred.

The reaction temperature employed in method B depends upon various factors such as the nature of the starting material and the solvent. However, it is usually between –10° C. and 150° C., and is preferably between 10° C. and 100° C.

The reaction time employed in method B depends on the reaction temperature and the like. However, it is usually from 5 minutes to 24 hours and preferably from 10 minutes to 10 hours.

In addition, when $R^9$ is t-butyl, the protecting group $R^9$ can be removed using an acid in the same procedure as described in step 2.

(Method C)

Compounds of formula (7a) wherein $R^{8e}$ is hydrogen are prepared by method C, wherein $R^{1e}$, $R^{2e}$, $R^{3e}$, $R^{4e}$, and $R^{7e}$ are as defined above.

Method C comprises reduction of the nitro group of a compound of formula (14) (which compound is referred to as compound (14) hereinafter). Method C can be accomplished by a similar procedure to the catalytic hydrogenation described in step 2, the process of which is the removal of an amino protecting group.

The desired compounds in method A, B and C can be isolated from the reaction mixture by a conventional technique, for example, when there is insoluble material in the reaction mixture, the reaction mixture is filtered, the filtrate, if necessary, is neutralized and cooled to afford the desired crystals which are collected by filtration or the solvent of the filtrate is evaporated off and the residue is partitioned between water and an organic solvent immiscible with water, the organic layer is dried over anhydrous magnesium sulfate and concentrated to give the desired product. The desired product thus isolated can be, if necessary, further purified through a conventional technique such as recrystallization or chromatography.

Compounds (13) which are starting materials in method B and compounds (14) which are starting materials in method C are known compounds or can be prepared according to a technique known to those skilled in the art (for example Japanese Patent Application Publication Hei 9-295970).

EXAMPLES

The following examples and reference examples are intended to further illustrate the present invention and are not intended to limit the scope of the invention in any way.

Example 1

N-(5-Methoxy-2-nitrophenyl)-N-t-butoxycarbonylcarbamic acid t-butyl ester (Exemplification Compound Number 1-2)

To a solution of 5-methoxy-2-nitroaniline (4.8 g) in ethyl acetate (70 ml) were added dimethylaminopyridine (177 mg) and di-t-butyl dicarbonate (13.9 g) and the mixture was stirred at 25° C. for 3 hours. At the end of this time the reaction mixture was cooled to room temperature and concentrated in vacuo to give the title compound (10.6 g, yield 101%).

IR spectrum (KBr, ν $cm^{-1}$): 2980, 1801, 1738, 1601, 1292, 1149, 843.

$^1$H-NMR spectrum (CDCl$_3$, 400 MHz, δ ppm): 1.38(18H, s), 3.87(3H, s), 6.75(1H, d, J=2.7 Hz), 6.91(1H, dd, J=9.2, 2.7 Hz), 8.12(1H, d, J=9.2 Hz).

Example 2

N-(2-Amino-5-methoxyphenyl)-N-methylcarbamic acid t-butyl ester (Exemplification Compound Number 5-8)

To a suspension of N-(5-methoxy-2-nitrophenyl)-N-methylcarbamic acid t-butyl ester (5.8 g) in toluene (55 ml) was added 7.5% palladium on carbon (1.2 g, which contain 50% water) and the air of the reaction vessel was replaced with nitrogen and the mixture was stirred under a hydrogen atmosphere at 40° C. for 3 hours. After the reaction the mixture was cooled to room temperature and the hydrogen in the reaction vessel was replaced with nitrogen. The palladium on carbon was removed by filtration and the filtrate was evaporated in vacuo to 22 ml. To this solution was slowly added methylcyclohexane (44 ml) and the precipitated crystals were filtered to give the title compound (4.4 g, yield 85%).

IR spectrum (KBr, ν $cm^{-1}$): 3369, 1685, 1673, 1513, 1379, 1227, 1168, 1042, 816.

$^1$H-NMR spectrum (CDCl$_3$, 400 MHz, δ ppm): 1.38(9H, br.s), 3.13(3H, s), 3.53(2H, br.s), 3.72(3H, s), 6.59–6.70(3H, m).

Example 3

N-[2-[4-(2,4-Dioxothiazolidin-5-ylmethyl)phenoxyacetylamino]-5-methoxyphenyl]-N-methylcarbamic acid t-butyl ester (Exemplification Compound Number 9-8)

To a suspension at 0° C. of N-(2-amino-5-methoxyphenyl)-N-methylcarbamic acid t-butyl ester (4.2 g) and 4-(2,4-dioxothiazolidin-5-ylmethyl)phenoxyacetic acid (5.2 g) in methylene chloride (30 ml) was added triethylamine (5.1 ml) and 50% propylphosphonic acid cyclic anhydride in ethyl acetate (12.7 g) and the mixture was stirred at the same temperature for 2 hours. At the end of this time to the reaction mixture was added 5% aqueous sodium hydrogencarbonate solution and the mixture was extracted with methylene chloride. The extract was washed with water and diluted hydrochloric acid and concentrated in vacuo. To the residue was added methanol (40 ml) and the precipitated crystals were filtered to give the title compound (7.3 g, yield 85%).

IR spectrum (KBr, ν $cm^{-1}$): 3323, 1751, 1697, 1534, 1510, 1232, 1153.

$^1$H-NMR spectrum (DMSO-d$_6$, 400 MHz, δ ppm): 1.28 (9H, br.s), 3.02(3H, s), 3.07(1H, dd, J=14.0, 9.1 Hz), 3.31 (1H, dd, J=14.0, 4.3 Hz), 3.74(3H, s), 4.65(2H, s), 4.87(1H, dd, J=9.1, 4.3 Hz), 6.80–6.95(2H, m), 6.92(2H, d, J=8.5 Hz), 7.19(2H, d, J=8.5 Hz), 7.69(1H, br.s), 8.95(1H, br.s), 12.00 (1H, br.s).

Example 4

N-(5-Methoxy-2-nitrophenyl)carbamic acid t-butyl ester

To a solution of N-(5-methoxy-2-nitrophenyl)-N-t-butoxycarbonylcarbamic acid t-butyl ester (10.6 g) in toluene (5 ml) and methanol (30 ml) was added 24% sodium methoxide in methanol (3.1 ml) and the mixture was stirred at 25° C. for 3 hours. At the end of this time the reaction mixture was cooled to 0° C. and the precipitated crystals were filtered to give the title compound (5.8 g, yield 75%).

IR spectrum (KBr, ν $cm^{-1}$): 1737, 1615, 1592, 1338, 1279, 1252, 1147.

$^1$H-NMR spectrum (CDCl$_3$, 400 MHz, δ ppm): 1.54(9H, s), 3.91(3H, s), 6.57(1H, dd, J=9.5, 2.8 Hz), 8.16(1H, d, J=2.8 Hz), 8.18(1H, d, J=9.5 Hz).

Example 5

5-[4-(6-Methoxy-1-methylbenzimidazol-2-ylmethoxy)benzyl]thiazolidin-2,4-dione monohydrochloride To a suspension of N-[2-[4-(2,4-dioxothiazolidin-5-ylmethyl)phenoxy-acetylamino]-5-methoxyphenyl]-N- methylcarbamic acid t-butyl ester (7.2 g) in methanol (82 ml) was added 2 mol/l hydrogen chloride-methanol (26 ml) and the mixture was heated under reflux for 4 hours. The reaction mixture was cooled to 40° C. and stirred at the temperature for 1 hour and cooled to 25° C. and then the precipitated crystals were filtered to give the title compound (5.4 g, yield 89%). melting point: 267–271° C.

IR spectrum(KBr, ν cm$^{-1}$): 1754, 1699, 1502, 1252, 1225, 1150, 823.

$^1$H-NMR spectrum (DMF-d$_7$, 400 MHz, δ ppm): 3.11(1H, dd, J=14.0, 9.0 Hz), 3.34(1H, dd, J=14.0, 4.0 Hz), 3.89(3H, s), 3.98(3H, s), 4.91(1H, dd, J=9.0, 4.0 Hz), 5.64(2H, s), 7.14(2H, d, J=9.0 Hz), 7.15(1H, d, J=9.0 Hz), 7.25(2H, d, J=9.0 Hz), 7.50(1H, s), 7.70(1H, d, 9.0 Hz), 12.04(1H, s).

Example 6

2-[4-(2,4-Dioxothiazolidin-5-ylmethyl)phenoxy]-N-(4-methoxy-2-methylaminophenyl)acetamide To a suspension at 0° C. of 4-methoxy-N$^2$-methyl-1,2-phenylenediamine di-hydrochloride (5.5 g) and 4-(2,4-dioxothiazolidin-5-ylmethyl)phenoxyacetic acid (7.6 g) in methylene chloride (55 ml) were added triethylamine (14.3 ml) and 50% propylsulfonic acid cyclic anhydride in ethyl acetate (18.7 g) and the mixture was stirred at 0° C. for 2.5 hours. At the end of this time, to the reaction mixture was added 5% aqueous sodium hydrogencarbonate solution and it was extracted with methylene chloride. The extract was washed with saturated aqueous sodium chloride solution and concentrated in vacuo to give the crude product (10.6 g). A suspension of the crude product (6.0 g) in methylene chloride (12.3 ml) was heated under reflux. To the solution was added ethanol (18.5 ml) and the mixture was cooled to 25° C. After 1 hour the solution was stirred at 0° C. for 30 minutes and the precipitated crystals were filtered to give the title compound (3.4 g, yield 63%)

IR spectrum (KBr, ν cm$^{-1}$): 3383, 1753, 1696, 1528, 1512, 1216, 830.

$^1$H-NMR spectrum (DMSO-d$_6$, 400 MHz, δ ppm): 2.67 (3H, d, J=4.8 Hz), 3.07(1H, dd, J=14.0, 9.1 Hz), 3.31(1H, dd, J=14.0, 4.1 Hz), 3.70(3H, s), 4.62(2H, s), 4.87(1H, dd, J=9.1, 4.1 Hz), 5.08(1H, d, J=4.8 Hz), 6.09(1H, d, J=8.4 Hz), 6.13(1H, dd, J=8.4, 2.7 Hz), 6.90(1H, d, J=8.4 Hz), 6.95(1H, d, J=8.7 Hz), 9.06(1H, s), 11.99(1H, br.s).

Example 7

5-[4-(6-Methoxy-1-methylbenzimidazol-2-ylmethoxy)benzyl]thiazolidin-2,4-dione mono-hydrochloride To a suspension of 2-[4-(2,4-dioxothiazolidin-5-ylmethyl)phenoxy-N-(4-methoxy-2-methylaminophenyl) acetamide (3.0 g) in methanol (46 ml) was added 2 mol/l hydrogen chloride-methanol (14 ml) and the mixture was heated under reflux for 4 hours. The reaction mixture was cooled to 40° C. and stirred at the same temperature for 1 hour. At the end of this time the reaction mixture was cooled to 25° C. and the precipitated crystals were filtered to give the title compound (2.9 g, yield 92%). Melting point, IR spectrum and NMR spectrum of this compound are substantially identical with those of the compound obtained in Example 5.

Comparative Example 1

N-tert-Butoxycarbonyl-5-methoxy-2-nitroaniline (Process for Preparation of the Compound Obtained in Reference Example 6 Disclosed in Japanese Patent Application Publication Hei-9-295970)

To a solution of 5-methoxy-2-nitroaniline (16 g) in anhydrous tetrahydrofuran (500 ml) were added di-tert-butyl dicarbonate (25 g), pyridine (15 ml) and 4-(dimethyl-amnino)pyridine (0.6 g) at room temperature and the mixture was stirred for 2 hours. The reaction mixture was concentrated and the residue was partitioned between ethyl acetate and water. The extract was washed with saturated aqueous sodium chloride solution and dried over anhydrous sodium sulfate and concentrated. The residue was purified by chromatography on a silica gel column using ethyl acetate: n-hexane=1:10 as the eluant to give the desired compound (12.5 g, yield 49%, melting point 112–114° C.).

Comparative Example 2

5-[4-(6-Methoxy-1-methylbenzimidazol-2-ylmethoxy)benzyl]thiazolidin-2,4-dione (Process for Preparation of the Compound Obtained in Example 2 Disclosed in Japanese Patent Application Publication Hei-9-295970)

A mixture of 5-methoxy-N-methyl-1,2-phenylenediamine (21.8 g), 5-(4-methoxycarbonylmethyloxybenzyl) thiazolidine-2,4-dione (63.4 g), 1,4-dioxane (250 mg) and concentrated hydrochloric acid (750 ml) was heated under reflux for 60 hours. The reaction mixture was cooled in an ice bath and the precipitated crystals were filtered. To the crystals were added 5% aqueous sodium hydrogencarbonate solution (800 ml) and the mixture was stirred at room temperature for 2 hours. The mixture was filtered and the insoluble material was collected by filtration and dissolved in a mixture of N,N-dimethylformamide (1000 ml) and methanol (200 ml) and decolorized with active charcoal. The active charcoal was removed by filtration and the filtrate was concentrated to about 50 ml. To the solution was added diethyl ether (750 ml) and allowed to stand at room temperature for 2 days. The precipitated crystals were filtered to give the desired product (20.1 g, yield 35%, melting point 267–271° C., Rf=0.68: chromatography on a silica gel thin layer using 5% ethanol-methylene chloride as the eluant).

As shown in the following scheme,

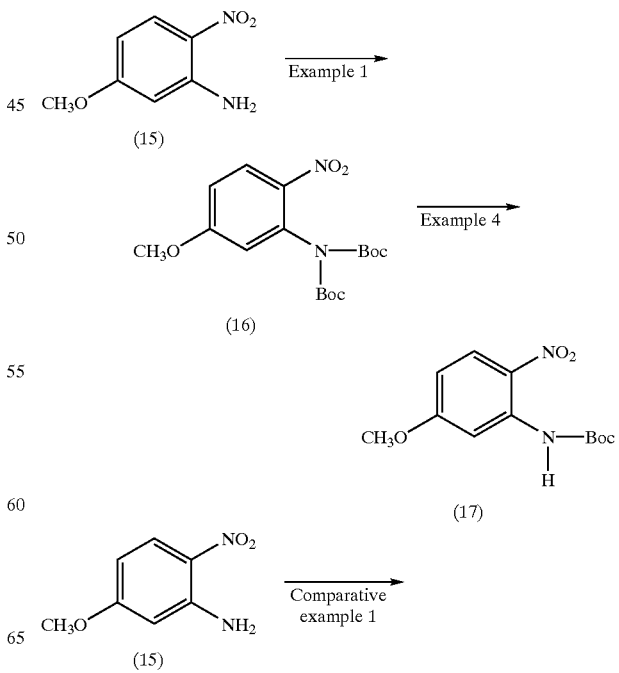

-continued

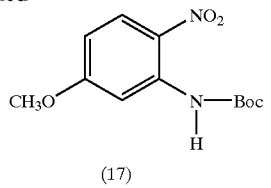

(17)

there are two processes for the preparation of the compound of formula (17) from the starting compound of formula (15), one of which is a two step reaction comprising of Examples 1 and 4 and the other one of which is the one step reaction of Comparative example 1. The total yield of compound (17) through the two step reaction (Examples 1 and 4) is 75%, on the other that of compound (17) through the one step reaction (Comparative example 1) is 49%. The yield of compound (17) through the two step reaction (Examples 1 and 4) is extremely improved in comparison with that of Comparative example 1. The process of this invention is a useful method for the synthesis of compound (17) which is an important intermediate for the preparation of the benzimidazole derivatives disclosed in Japanese Patent Application Publication Hei-9-295970.

Compound (1), which encompasses the compound of formula (16) which is an intermediate of the process described in the above Examples, is a useful intermediate in preparing the benzimidazole derivatives disclosed in Japanese Patent Application Publication Hei-9-295970.

In addition, as shown in the following scheme,

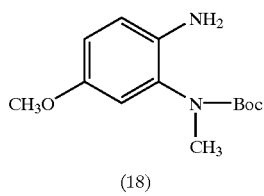 + 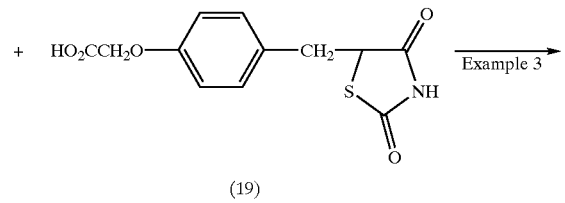 Example 3

(18)                    (19)

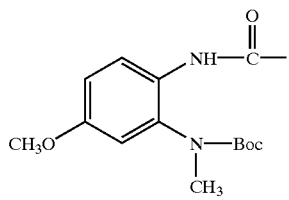 Example 5

(20)

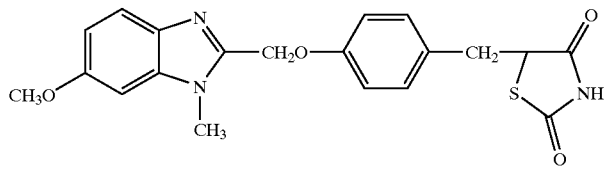

(21)

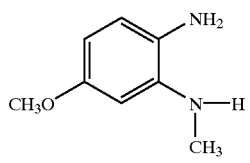 + 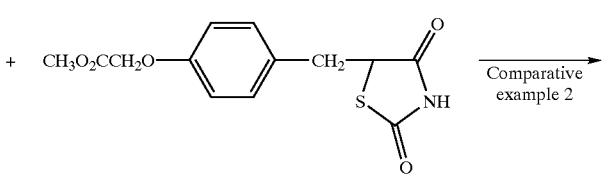 Comparative example 2

(22)                    (23)

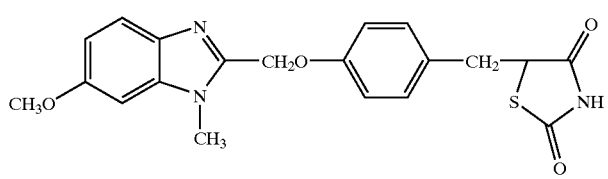

(24)

there are two processes for the preparation of benzimidazole derivatives through the reaction of an amine derivative with a thiazolidinedione derivative. One of these is a two step reaction, that is Examples 3 and 5 and the other is a one step reaction, that is Comparative example 2. The total yield of the two step reaction (Examples 3 and 5) is 76%, on the other the yield of the one step reaction (Comparative example 2) is 35%. The total yield of the two step reaction (Examples 3 and 5) is extremely improved in comparison with that of the one step reaction (Comparative example 2). The process of this invention is a useful method for the synthesis of benzimidazole derivatives disclosed in Japanese Patent Application Publication Hei-9-295970.

In the process for preparation of Examples 3 and 5, compound (2), which encompasses the compound of formula (18) which is a staring compound, and compound (3), which encompasses the compound of formula (20), which is an intermediate, are useful intermediates in preparing the benzimidazole derivatives disclosed in Japanese Patent Application Publication Hei-9-295970.

Reference Example 1

5-Methoxy-2-nitroaniline

To a solution of 5-chloro-2-nitroaniline (5.0 g) in dimethylformamide (25 ml) was added 24% sodium methoxide in methanol (11 ml) and the mixture was heated at 80° C. for 4 hours. At the end of this time, the reaction mixture was cooled to room temperature and partitioned between ethyl acetate and water. The extract was washed with 20% aqueous sodium chloride solution and insoluble material was filtered off. The filtrate was concentrated in vacuo to give the desired compound (4.8 g, yield 99%).

IR spectrum (KBr, $\nu$ cm$^{-1}$): 3477, 3362, 1626, 1412, 1245, 1108, 830.

$^1$H-NMR spectrum (CDCl$_3$, 400 MHz, $\delta$ ppm): 3.82(3H, s), 6.15(1H, d, J=2.7 Hz), 6.21(2H, br.s), 6.28(1H, dd, J=9.5, 2.7 Hz), 8.06(1H, d, J=9.5 Hz).

Reference Example 2

N-(5-Methoxy-2-nitrophenyl)-N-methylcarbamic acid t-butyl ester

To a solution at 0° C. of N-(5-methoxy-2-nitrophenyl) carbamic acid t-butyl ester (5.5 g) in dimethylformamide (35 ml) was added sodium hydride (0.9 g, 60% dispersion in mineral oil) and the mixture was stirred at 0° C. for 1 hour. A solution of dimethyl sulfate (2.2 ml) in dimethylformamide (5.5 ml) was slowly added dropwise at 0° C. and the mixture was stirred at the same temperature for 0.5 hours. At the end of this time, to the reaction mixture was slowly added water (55 ml) and the mixture was extracted with toluene (66 ml). The extract was washed with water and concentrated in vacuo to give the desired compound (5.8 g, yield 100%).

IR spectrum (KBr, $\nu$ cm$^{-1}$): 1709, 1605, 1591, 1341, 1240, 1153.

$^1$H-NMR spectrum (CDCl$_3$, 400 MHz, $\delta$ ppm): 1.30(9H, s), 3.28(3H, s), 3.89(3H, s), 6.77(1H, d, J=2.7 Hz), 6.82(1H, dd, J=9.0, 2.7 Hz), 7.97(1H, d, J=9.0 Hz).

Reference Example 3

5-Methoxy-N-methyl-2-nitroaniline

To a solution at 0° C. of 5-chloro-2-nitroaniline (100 g) in dimethylformamide (1.0 l) was added potassium t-butoxide (70.3 g) and the mixture was stirred at 0° C. for 1 hour. To the reaction mixture was added dropwise a solution of dimethyl sulfate (62 ml) in dimethylformamide (100 ml) and the resulting mixture was stirred at 25° C. for 1.5 hours to afford a solution of 5-chloro-N-methyl-2-nitroaniline in dimethylformamide. To the resulting mixture was added 24% sodium methoxide in methanol (230 ml) and the mixture was heated at 55° C. for 2 hours with stirring. At the end of this time the reaction mixture was cooled to 25° C. and water (1.5 l) was added. The precipitated crystals were collected by filtration and washed with water and methanol to give the desired compound (94.5 g, yield 90%).

IR spectrum (KBr, $\nu$ cm$^{-1}$): 3381, 1631, 1584, 1237, 1047, 819.

$^1$H-NMR spectrum (CDCl$_3$, 400 MHz, $\delta$ ppm): 2.98(3H, d, J=5.1 Hz), 3.86(3H, s), 6.10(1H, d, J=2.7 Hz), 6.21(1H, dd, J=9.5, 2.7 Hz), 8.11(1H, d, J=9.5 Hz), 8.26(1H, br.s).

Reference Example 4

4-Methoxy-N$^2$-methyl-1,2-phenylenediamine dihydrochloride

To a solution of 5-methoxy-N-methyl-2-nitroaniline (50 g) in ethyl acetate (500 ml) was added 7.5% palladium on carbon (5.0 g, containing 50% water) and the air in the reaction vessel was replaced with nitrogen. Then the mixture was allowed to absorb hydrogen at 20° C., the temperature was raised to 50° C. and this mixture was stirred at the same temperature for 2 hours. The mixture was cooled to 25° C. and the hydrogen in the vessel was replaced with nitrogen. The palladium on carbon was removed by filtration and the filtrate was concentrated in vacuo to 300 ml. To the residue were added methanol (150 ml) and 4 mol/l hydrogen chloride-ethyl acetate (200 ml) and the mixture was stirred at 25° C. for 30 minutes. The precipitated crystals were filtered to give the desired compound (60.3 g, yield 98%).

IR spectrum (KBr, $\nu$ cm$^{-1}$): 3346, 2842, 1625, 1522, 1301, 1222, 1105, 822.

$^1$H-NMR spectrum (DMSO-d$_6$, 400 MHz, $\delta$ ppm): 2.71 (3H, s), 3.71(3H, s), 6.24–6.32(2H, m), 7.15–7.22(1H, m), 9.37(5H, br.s).

Reference Example 5

4-(2,4-Dioxo-3-tritylthiazolidin-5-ylmethyl) phenoxyacetic acid t-butyl ester

To a solution of 5-(4-hydroxybenzyl)-3-tritylthiazolidin-2,4-dione (20.0 g) in acetonitrile (200 ml) was added cesium carbonate (21.0 g), followed by bromoacetic acid t-butyl ester (7.4 ml) and the mixture was stirred at 25° C. for 3 hours. To the reaction mixture was added water and the organic layer was separated and concentrated in vacuo. The residue was extracted with toluene and the extract was washed with diluted hydrochloric acid and water and concentrated in vacuo to give the desired compound (24.9 g).

IR spectrum (KBr, $\nu$ cm$^{-1}$): 1754, 1691, 1512, 1300, 1218, 1155, 740.

$^1$H-NMR spectrum (CDCl$_3$, 400 MHz, $\delta$ ppm): 1.48(9H, s), 3.04(1H, dd, J=14.2, 9.0 Hz), 3.43(1H, dd, J=14.2, 3.9 Hz), 4.36(1H, dd, J=9.0, 3.9 Hz), 6.83(2H, d, J=8.5 Hz), 7.11(2H, d, J=8.5 Hz), 7.15–7.35(15H, m).

Reference Example 6

4-(2,4-Dioxothiazolidin-5-ylmethyl)phenoxyacetic acid

To a solution of 4-(2,4-dioxo-3-tritylthiazolidin-5-ylmethyl)phenoxyacetic acid t-butyl ester (6.2 g) in toluene (25 ml) was added p-toluenesulfonic acid mono-hydrate (204 mg) and the mixture was heated under reflux for 3 hours. At elevated temperature ethyl acetate (10 ml) was added and the mixture was stirred at 25° C. for 1.5 hours. The precipitated crystals were filtered to give the desired compound (2.5 g).

IR spectrum(KBr, ν cm$^{-1}$): 3435, 3011, 1753, 1693, 1513, 1244, 1203.

$^1$H-NMR spectrum (DMSO-d$_6$, 400 MHz, δ ppm): 3.04 (1H, dd, J=14.2, 9.0 Hz), 3.30(1H, dd, J=14.2, 4.3 Hz), 4.63(2H, s), 4.86(1H, dd, J=9.0, 4.3 Hz), 6.84(2H, d, J=8.7 Hz), 7.15(2H, d, J=8.7 Hz), 11.20(1H, s), 12.94(1H, br.s).

This invention provides a process for the preparation of known benzimidazole derivatives or pharmaceutically acceptable salts thereof (for example Japanese Patent Application Publication Hei-9-295970 or corresponding U.S. Pat. No. 5,886,014) which exhibit excellent hypoglycemic activity; said process is useful in the large scale production of the benzimidazole derivatives. In large scale production according to this process, the desired compounds can be readily obtained in good yield and adequate purity using cheap reagents by simple procedures.

What is claimed is:

1. A process for the preparation of a compound of formula (5) or a pharmaceutically acceptable salt thereof by a reaction of compound (4) with alkali metal alkoxide,

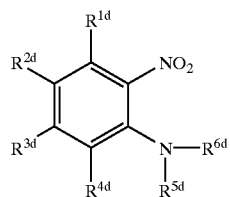

(4)

wherein $R^{1d}$, $R^{2d}$, $R^{3d}$ and $R^{4d}$ are each independently hydrogen, hydroxyl, $C_1$–$C_6$ alkyl, $C_1$–$C_6$ alkoxy, benzyloxy, acetoxy, trifluoromethyl or halogen, and $R^{5d}$ and $R^{6d}$ are each an amino protecting group,

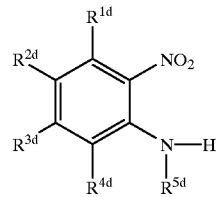

(5)

wherein $R^{1d}$, $R^{2d}$, $R^{3d}$, $R^{4d}$, and $R^{5d}$ are as defined above.

2. A process for the preparation of a compound or a pharmaceutically acceptable salt thereof according to claim 1 wherein $R^{5d}$ and $R^{6d}$ are each t-butoxycarbonyl, benzyloxycarbonyl, p-methoxybenzyloxycarbonyl or p-bromobenzyloxycarbonyl.

3. A process for the preparation of a compound or a pharmaceutically acceptable salt thereof according to claim 1 wherein $R^{5d}$ and $R^{6d}$ are each t-butoxycarbonyl.

4. A process for the preparation of a compound or a pharmaceutically acceptable salt thereof according to claim 1 wherein $R^{1d}$, $R^{2d}$, $R^{3d}$ and $R^{4d}$ are each independently hydrogen or $C_1$–$C_4$ alkoxy.

5. A process for the preparation of a compound or a pharmaceutically acceptable salt thereof according to claim 1 wherein $R^{1d}$, $R^{2d}$, $R^{3d}$ and $R^{4d}$ are each independently hydrogen or methoxy.

6. A process for the preparation of a compound or a pharmaceutically acceptable salt thereof according to claim 1 wherein $R^{1d}$, $R^{2d}$ and $R^{4d}$ are each hydrogen, $R^{3d}$ is methoxy, and $R^{5d}$ and $R^{6d}$ are each t-butoxycarbonyl.

* * * * *